(12) United States Patent
Irazoqui et al.

(10) Patent No.: US 11,191,962 B2
(45) Date of Patent: Dec. 7, 2021

(54) STIMULUS COIL AND PULSE GENERATOR FOR WIRELESS GLAUCOMA THERAPY

(71) Applicant: Purdue Research Foundation, West Lafayette, IN (US)

(72) Inventors: Pedro P. Irazoqui, West Lafayette, IN (US); Gabriel Simon, West Lafayette, IN (US); Gabriel O. Albors, Indianapolis, IN (US); Jack Williams, Lafayette, IN (US); Quan Yuan, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 146 days.

(21) Appl. No.: 16/351,251

(22) Filed: Mar. 12, 2019

(65) Prior Publication Data

US 2019/0275326 A1  Sep. 12, 2019

Related U.S. Application Data

(60) Provisional application No. 62/641,981, filed on Mar. 12, 2018.

(51) Int. Cl.
*A61N 1/04* (2006.01)
*A61N 1/36* (2006.01)
(Continued)

(52) U.S. Cl.
CPC ......... *A61N 1/36046* (2013.01); *A61N 1/025* (2013.01); *A61N 1/0408* (2013.01);
(Continued)

(58) Field of Classification Search
CPC .. A61N 1/36046; A61N 1/025; A61N 1/0408; A61N 1/0472; A61N 1/37223;
(Continued)

(56) References Cited

U.S. PATENT DOCUMENTS

| 4,271,841 A | 6/1981 | Friedman |
| 4,603,697 A | 8/1986 | Kamerling |

(Continued)

FOREIGN PATENT DOCUMENTS

| WO | WO 2005072294 | 8/2005 |
| WO | WO 2009150688 | 12/2009 |

(Continued)

OTHER PUBLICATIONS

Ahmed [online], "Addendum viii," Nov. 1993, [retrieved on Nov. 6, 2018], retrieved from: URL <https://www.accessdata.fda.gov/cdrh_docs/pdf/K925636.pdf>, 7 pages.

(Continued)

*Primary Examiner* — Rex R Holmes
(74) *Attorney, Agent, or Firm* — Fish & Richardson P.C.

(57) ABSTRACT

An improved stimulus coil for use in wireless stimulation of biological tissue (e.g., nerves, muscle tissue, etc.) and, in one exemplary implementation, to glaucoma therapy based on the wireless administration of energy to the eye of a mammalian subject (e.g., human, rodent, etc.) to reduce an elevated intraocular pressure (IOP) involving the use of an improved stimulus coil. The improved stimulus coil may be implanted in the eye of a mammalian subject or positioned on the exterior of the eye, such as (by way of example) by being disposed within a contact lens worn by a mammalian subject.

8 Claims, 19 Drawing Sheets

(51) Int. Cl.
  A61N 1/02    (2006.01)
  G02C 7/04    (2006.01)
  G02C 11/00   (2006.01)
  H02J 50/10   (2016.01)
(52) U.S. Cl.
  CPC ............. A61N 1/0472 (2013.01); G02C 7/04 (2013.01); G02C 11/10 (2013.01); H02J 50/10 (2016.02)
(58) Field of Classification Search
  CPC .... A61N 1/37229; A61N 1/3787; G02C 7/04; G02C 11/10; H02J 50/10
  See application file for complete search history.

(56) References Cited

U.S. PATENT DOCUMENTS

| | | | |
|---|---|---|---|
| 4,614,193 | A | 9/1986 | Liss et al. |
| 6,443,893 | B1 | 9/2002 | Schnakenberg |
| 7,282,046 | B2 | 10/2007 | Simon |
| 8,128,588 | B2 | 3/2012 | Coroneo |
| 8,267,882 | B2 | 8/2012 | Euteneuer et al. |
| 8,415,364 | B2 | 4/2013 | Epstein et al. |
| 8,419,673 | B2 | 4/2013 | Rickard |
| 2002/0013545 | A1 | 1/2002 | Soltanpour et al. |
| 2002/0127144 | A1 | 9/2002 | Mehta |
| 2005/0070987 | A1 | 3/2005 | Erickson |
| 2006/0122660 | A1 | 6/2006 | Boveja et al. |
| 2006/0224215 | A1 | 10/2006 | Pattern et al. |
| 2007/0027494 | A1 | 2/2007 | Gerber et al. |
| 2007/0027537 | A1 | 2/2007 | Castillejos |
| 2007/0255364 | A1 | 11/2007 | Gerber et al. |
| 2007/0284205 | A1 | 12/2007 | Wong et al. |
| 2008/0269833 | A1 | 10/2008 | Scott et al. |
| 2010/0222686 | A1 | 9/2010 | Fisher et al. |
| 2010/0228079 | A1 | 9/2010 | Forsell |
| 2011/0022118 | A1 | 1/2011 | Rickard |
| 2011/0238133 | A1* | 9/2011 | Gross .................. A61N 1/0526 607/53 |
| 2013/0006326 | A1* | 1/2013 | Ackermann ....... A61N 1/36046 607/53 |
| 2013/0030415 | A1 | 1/2013 | Goodman |
| 2013/0941153 | | 7/2013 | Irazoqui et al. |
| 2013/0293025 | A1 | 11/2013 | Xu et al. |
| 2014/0074186 | A1 | 3/2014 | Faltys et al. |
| 2014/0213843 | A1 | 7/2014 | Pilla et al. |
| 2017/0007834 | A1 | 1/2017 | Pedro et al. |

FOREIGN PATENT DOCUMENTS

| | | |
|---|---|---|
| WO | WO 2013063111 | 5/2013 |
| WO | WO 2015157725 | 10/2015 |
| WO | WO 2016059556 | 4/2016 |

OTHER PUBLICATIONS

Akay, "Long-term measurement of muscle denervation and locomotor behavior in individual wild-type and ALS model mice," Journal of Neurophysiology, Feb. 2014, 111:694-703.

Bernardi et al, "Specific absorption rate and temperature increases in the head of a cellular-phone user," Microwave Theory and Techniques, 2000, 48:1118-1126.

Braendstrup [online], "Muscular bio stimulator (2nd version)," May 2011, available: http://www.redcircuits.com/Page124.htm.

Brown et al, "Stimulus-artifact elimination in a multi-electrode system," Biomed Circuits Syst, Mar. 2008, 2:10-21.

Chandler, "Key needs and opportunities for treating glaucoma," Investigative Ophthalmology and Visual Science, May 2012, vol. 53, pp. 2456-2460.

Constable & Lim, Color Atlas of Ophthalmology. World Scientific Publishing Company, 1995.

DeLuca, "Draft guidance for industry and fda staff: Class ii special controls guidance document: Powered muscle stimulator for rehabilitation," CDRH, Apr. 5, 2010, 19 pages.

Detry-Morel, "Side effects of glaucoma medications," Bull. Soc. Belge Ophthal, 2006, vol. 299, pp. 27-40.

Dietlein, "The medical and surgical treatment of glaucoma," Dtsch Arztebl Int, 2009, vol. 116, pp. 597-606.

EP Extended European Search Report in EP Appln. No. EP17811170, dated May 22, 2019, 7 pages.

EP Supplementary Partial European Search Report in European Appln. No. 17816256, dated Jun. 14, 2019, 16 pages.

FDA [online], "Tomey dtl electrode," May 1997, [retrieved on Nov. 6, 2018], retrieved from: URL <https://www.accessdata.fda.gov/scripts/cdrh/cfdocs/cfPMN/pmn.cfm?ID=K961805>, 1 page.

FDA, "Guidance for industry and for fda reviewers/staff—guidance on 510(k) submissions for keratoprostheses," Mar. 1999, 11 pages.

Fechter, "Improvised 3-0 polypropylene plug for the glaucoma drainage tube during phacoemulsification," Ophthalmic. Surg. Lasers Imaging, Jan./Feb. 2008, vol. 39, pp. 86-87.

Fernandes et al, "Artificial vision through neuronal stimulation," Neuroscience Letters, Jun. 25, 2012, vol. 519, pp. 122-128.

Foster[online], "Specific questions related to glaucoma," available on or before Oct. 7, 2013, via Internet Archive: Wayback Machine Url : <https://web.archive.org/web/20131007014544/http://www.rcophth.ac.uk/page.asp?section=373&sectionTitle=Specific+Questions+Related+to+Glaucoma>, [retrieved on Nov. 6, 2018], retrieved from: URL <http://www.rcophth.ac.uk/page.asp?section=373&sectionTitle=Specific+Questions+Related+to+Glaucoma>, 1 page.

G. R. Foundation [online], "Glaucoma facts and stats," Aug. 2013, [retrieved on Nov. 5, 2018], retrieved from: <http://www.glaucoma.org/glaucoma/glaucoma-facts-and-stats.php>, 3 pages.

G. Technologies [online], "Sd9 square pulse stimulator," available on or before Jul. 7, 2013, via iInternet Archive: Wayback Machine URL <https://web.archive.org/web/20130707155649/http://www.grasstechnologies.com/products/stimulators/stimsd9.html>, [retrieved Nov. 6, 2018], retrieved from: URL <http://www.grasstechnologies.com/products/stimulators/stimsd9.html>, 2 pages.

Ghosh et al., "Lens-solution interactions: Impact on biocompatibility," Presented at The 15th Symposium on the Material Science and Chemistry of Contact Lenses. Center for Devices and Radiological Health, FDA, Mar. 18, 2011, 43 pages.

Ghovanloo & Najafi, "A Compact Large Voltage-Compliance High Output-Impedance Programmable Current Source for Implantable Microstimulators," Biomedical Engineering, 2005, 52:97-105.

Glaucoma Research Foundation [online], "Laser surgery," Aug. 25, 2017, [retrieved on Nov. 6, 2018], retrieved from: URL <http://www.glaucoma.org/treatment/laser-surgery.php>, 3 pages.

Greenwell and Spillman, "Use of medicated drops and oral tablets in glaucoma treatment," Curr Opin Ophthalmol., Apr. 1996, vol. 7, pp. 44-46.

International Commission on Non-Ionizing Radiation, "Guidelines for limiting exposure to time-varying electric and magnetic fields (1 Hz to 100 kHz)," Health Phys, Dec. 2010, 99:818-36.

Janunts, "Optical remote sensing of intraocular pressure by an implantable nanostructured array," available: http://www.uniklinikum-saarland.de/en/facilities/departments and institutes/experimentalophthalmology/research/iop sensing/.

Jefferys et al., "Chronic focal epilepsy induced by intracerebral tetanus toxin," The Italian Journal of Neurological Sciences, 1995, 16:27-32.

Jolin M. Eisenberg Center for Clinical Decisions and Communications Science, "Comparisons of medical, laser, and incisional surgical treatments for open-angle glaucoma in adults," AHRQ, 2012, 4 pages.

Keenan, [online], "510(k) summary," Nov. 28, 2008, [retrieved on Nov. 6, 2018], retrieved from: URL <https://www.accessdata.fda.gov/cdrh_docs/pdf8/K082011.pdf>, 7 pages.

King et al, Clinical review: Glaucoma, BMJ, Jun. 15, 2013, vol. 346, pp. 29-33.

Kobayashi et al., "Accuracy of intraocular pressure by tono-pen xl over amniotic membrane patching in rabbits," American Journal of Ophthalmology, Apr. 2003, vol. 135, pp. 536-537.

(56) References Cited

OTHER PUBLICATIONS

Kok & Barton, "Uveitic glaucoma," Ophthalmol Clin North Am, vol. 15, pp. 375-387, 2002.

Lee et al, "Primary acute angle closure: long-term clinical outcomes over a 10 year period in the chinese population," Apr. 2014, vol. 34, pp. 165-169.

Lewinstein et al., "Antibacterial properties of aged dental cements evaluated by direct-contact and agar diffusion tests," Journal of Prosthetic Dentistry, Apr. 2005, vol. 93, pp. 364-371.

Loeb & Peck, "Cuff electrodes for chronic stimulation and recording of peripheral nerve activity," J Neurosci Methods, Jan. 1996, 64:95-103.

Lu et al, "Electrical stimulation with a penetrating optic nerve electrode array elicits visuotopic cortical responses in cats." J Neural Eng, Jun. 2013, vol. 10, pp. 1-11.

Lusby et al [online], "Glaucoma," Sep. 2011, [retrieved on Nov. 5, 2018], retrieved from: <http://www.nlm.nih.gov/medlineplus/ency/article/001620.htm>, 8 pages.

Managed Care Eye Institute [online], "Coats of the eye: Ciliary body," Jan. 2012, [retrieved on Nov. 5, 2018], retrieved from: <http://teaching.pharmacy.umn.edu/courses/eyeAP/Eye_Anatomy/CoatsoftheEye/CiliaryBody.htm>, 1 page.

Mayo Clinic Staff [online], "Glaucoma: Treatment and drugs," Oct. 2012, available: [retrieved on Nov. 5, 2018], retrieved from <:www.mayoclinic.com/health/glaucoma/DS00283/DSECTION=treatments-and-drugs>, 5 pages.

Mei et al, "Optimal Wireless Power Transfer to Systems in an Enclosed Resonant Cavity," IEEE Antennas and Wireless Propagation Letters, 2015, 4 pages.

Mei et al., "Cavity Resonator Wireless Power Transfer System for Freely-Moving Animal Experiments," IEEE Transactions on Biomedical Engineering, 2015.

Moorthy, "Glaucoma associated with uveitis," Surv Ophthalmol, 1997, pp. 361-394.

Mountaintop Medical, "Advances in opthamology: Markets in the treatment of eye disorders and corrective vision," Jul. 2009.

Murgatroyd & Bembridge, "Intraocular pressure," Oxford Journal of Medicine, 2008, vol. 8, pp. 100-103.

Nesterov & Khadikova [online], "Effect of ciliary muscle electrical stimulation on ocular hydrodynamics and visual function in patients with glaucoma," Vestn Oftalmol., 1997, vol. 113, pp. 12-14 [English Abstract].

Optonol Ltd [online], "Summary of safety & effectiveness," Mar. 1, 2003, [retrieved on Nov. 6, 2018], retrieved from: URL <https://www.accessdata.fda.gov/cdrh_docs/pdf3/K030350.pdf>, 5 pages.

Optonol Ltd. [online], "510(k) summary," Mar. 2002, [retrieved on Nov. 6, 2018], retrieved from: URL <https://www.accessdata.fda.gov/cdrh_docs/pdf/K012852.pdf>, 7 pages.

Panarelli et al, "Scleral stula closure at the time of glaucoma drainage device tube repositioning: a novel technique," Arch Ophthalmol., Nov. 2012, vol. 130, pp. 1447-1451.

PCT International Preliminary Report on Pattentability in Appln. No. PCT/US2017/037079, dated Dec. 11, 2018, 18 pages.

PCT International Search Report and Written Opinion in International Appln. No. PCT/US2017/038879, dated Sep. 27, 2017, 15 pages.

PCT International Search Report and Written Opinion in International Appln. No. PCT/US2017/37079, dated Nov. 13, 2017, 30 pages.

Pearson et al, "A new electrode configuration for recording electromyographic activity in behaving mice," J Neurosci Methods, Oct. 15, 2005, 148:36-42.

Pescosolido et al, "Role of dopaminergic receptors in glaucomatous disease modulation," Biomed. Res. Int., 2013, 5 pages.

Pham & Hu, "Cytotoxicity evaluation of multipurpose contact lens solutions using an in vitro test battery," CLAO Journal, Jan. 1999, vol. 25.

Porcari et al, "Effects of electrical muscle stimulation on body composition, muscle strength, and physical appearance," Journal of Strength and Conditioning Research, 2002, vol. 16, pp. 165-172.

Quigley & Vitale, "Models of open-angle glaucoma prevalence and incidence in the United States," Investigative Ophthalmology and Visual Science, Jan. 1997, vol. 38, pp. 83-91.

Shahrokhi et al, "The 128-channel fully differential digital integrated neural recording and stimulation interface," Biomedical Circuits and Systems, 2010, 4:149-161.

Shields, Shields textbook of glaucoma. Philadelphia, PA: Lippincott Williams & Wilkins, 2005.

Sjogren and Dahl, "Cytotoxicity of dental alloys, metals, and ceramics assessed by millipore filter, agar overlay, and mtt tests," Elsevier, Aug. 2000, vol. 84, pp. 229-236.

Sun et al, "Spatiotemporal properties of multipeaked electrically evoked potentials elicited by penetrative optic nerve stimulation in rabbits," Investigative Ophthalmology and Visual Science, Aug. 2010, vol. 52, pp. 146-154.

Texas Instruments, "Lm741 operational amplifier," Mar. 2013, 11 pages.

U. Z. Leuven [online], Validation of retinal oximetry in glaucoma patients: a structural and functional correlation, Feb. 2013 [retrieved on Nov. 5, 2018], retrieved from: <http://www.clinicaltrials.gov/ct2/show/NCT01391247?term=glaucoma&rank=13>, 6 pages.

US food and Drug Administration [online], "Classify your medical device," Dec. 2012, available on or before Apr. 17, 2018, via Internet Archive: Wayback Machine URL: <https://web.archive.org/web/20180417153853/http://www.fda.gov/MedicalDevices/DeviceRegulationandGuidance/Overview/ClassifyYourDevice/>, [retrieved on Nov. 6, 2018], retrieved from: URL <http://www.fda.gov/MedicalDevices/DeviceRegulationandGuidance/Overview/ClassifyYourDevice/>, 3 pages.

V. E. S. Center [online], "Ahmed valve glaucoma implant with adjunctive subconjunctival bevacizumab in refractory glaucoma," May 2010, available: http://www.clinicaltrials.gov/ct2/show/NCT01128699?term=glaucoma&rank=15>, 6 pages.

Valk, "Intraocular pressure-lowering effects of all commonly used glaucoma drugs: a meta-analysis of randomized clinical trials," Ophthalmology, 2005, vol. 112, pp. 1177-1185.

Wang et al, "Intervention of laser periphery iridectomy to posterior iris bowing in high myopic eyes," Chin. Med. J. (Engl)., Dec. 2012, vol. 125, pp. 4466-4469.

Wong & Graham, "Effect of repeat use and coating defects of gold foil electrodes on electroretinogram recording," Vision Research, 1995, vol. 35, pp. 2795-2799.

\* cited by examiner

S4-A: 5-Turns Coil

S4-B: 6-Turns Coil

S4-C: Strain test coil-6 turn

STIMULUS COIL AND PULSE GENERATOR FOR WIRELESS GLAUCOMA THERAPY

CROSS-REFERENCE TO RELATED APPLICATIONS

This application claims the benefit of U.S. Provisional Application Ser. No. 62/641,981, filed on Mar. 12, 2018, the contents of this aforementioned application being fully incorporated herein by reference.

BACKGROUND

The present invention relates generally to wireless stimulation of biological tissue (e.g., nerves, muscle tissue, etc.) and, in one exemplary implementation, to therapy for glaucoma based on the wireless administration of energy to the eye of a mammalian subject (e.g., human, rodent, etc.) to reduce an elevated intraocular pressure (IOP) involving the use of an improved stimulus coil for use with a multi-coil wireless power transfer assembly having an improved pulse generator. The improved stimulus coil may be used alone or in combination with a contact lens for placement adjacent to the exterior of an eye of a mammalian patient. The improved stimulus coil may also be implanted in the eye of a mammalian subject.

Glaucoma is currently the leading cause of blindness and continues to cause blindness in around 10% of even those patients who receive the most up to date treatment. The primary cause of glaucoma is an excess of intraocular pressure (IOP) which presses on and damages the optic nerve. In a normally functioning mammalian eye, fluid (namely, aqueous humor) is pumped into the anterior segment of the eye to, among other things, maintain a healthy IOP and provide nutrients to the structures in the anterior segment. The fluid is then drained out primarily through the drainage tissues at the junction of the cornea and iris in the region of the eye known as the limbus. In glaucoma, an elevated IOP results from an excess of aqueous humor which may be due to a combination of a) the ciliary body producing too much fluid (increased inflow) and/or b) too much resistance to aqueous humor drainage out of the eye (limited outflow) depending upon the type of glaucoma.

Glaucoma may take many forms. Open-angle glaucoma is where the aqueous humor does not drain as quickly due to abnormal resistance in the trabecular meshwork and Schlemm's canal pathway. The increase in IOP in open-angle glaucoma is usually a slow process and generally does not exhibit any symptoms. When vision starts to decrease, severe damage has already been done to the optic nerve. Closed-angle (sometimes referred to as "Angle-closure glaucoma") is where the aqueous humor does not drain from the eye because of a blockage or resistance in the trabecular network by the iris. This causes a sudden spike in the intraocular pressure and is considered an emergency. Congenital glaucoma is a birth defect caused by abnormal eye development. Secondary glaucoma is caused by external factors such as drugs, disease, or trauma. Open-angle glaucoma is the most common form of glaucoma and has a clear genetic component. When considered in all forms, the populations of patients with glaucoma or high IOP (pre-glaucoma) are predicted to grow steadily due to, among other reasons, the demographic increase in the aging population.

Existing medical and surgical treatments attempt to reduce IOP to non-damaging levels by targeting either the drainage or production of aqueous humor, but with limited success. The two primary approaches include the use of eye-drops to regulate fluid flow and surgeries to open drainage channels in the eye. The pharmacological (eye-drop) methods for reducing IOP in glaucoma and ocular hypertensive patients provide only acute relief of symptoms for the chronic disease. The surgical approaches have largely focused on implanting a stent or similar structure to wick or facilitate the drainage of aqueous humor. Laser surgical approaches achieve a similar same effect as stents by creating or increasing openings in the drainage region of the eye. Bleb surgeries create an opening out of the anterior chamber to facilitate drainage. Such surgical approaches have enjoyed limited clinical success for a host of reasons, including the increased risk of infection due to the bacterial pathway that exists by virtue of the physical drainage element (e.g. bleb) extending outside the eye during use. The same infection risk is present for the prior art efforts involving the use of electrical stimulation of the eye to reduce IOP, which typically include hard-wired electrodes with leads extending from the eye during use.

There is a need to develop a method to chronically reduce IOP of all patients with glaucoma or ocular hypertension to a safe level without causing unacceptable side effects.

SUMMARY

The details of one or more embodiments of the subject matter described in this specification are set forth in the accompanying drawings and the description below. Other features, aspects, and advantages of the invention will become apparent from the description, the drawings, and the claims.

In some implementations, a device for reducing elevated intraocular pressure in an eye of a mammalian subject includes an improved stimulation electrode assembly adapted to be positioned at least one of on, within, and near the eye of the mammalian subject. The improved stimulation electrode assembly is passive, meaning it is configured to receive a stimulation signal from a wireless power transfer system and deliver the stimulation signal to at least one intraocular structure in a therapeutically effective amount to reduce the elevated intraocular pressure within a mammalian eye by (i) decreasing aqueous humor inflow into an anterior segment of the eye, and (ii) increasing aqueous humor outflow from the anterior segment of the eye.

In some implementations, a method of reducing elevated intraocular pressure in an eye of a mammalian subject includes transmitting an electromagnetic field to an improved stimulation electrode assembly positioned at least one of on, within, and near the eye of a mammalian subject. The stimulation electrode assembly is adapted to stimulate at least one intraocular structure to reduce an elevated intraocular pressure within the mammalian eye by (i) decreasing aqueous humor inflow into an anterior segment of the eye, and (ii) increasing aqueous humor outflow from the anterior segment of the eye.

DRAWING DESCRIPTIONS

Figure 16:
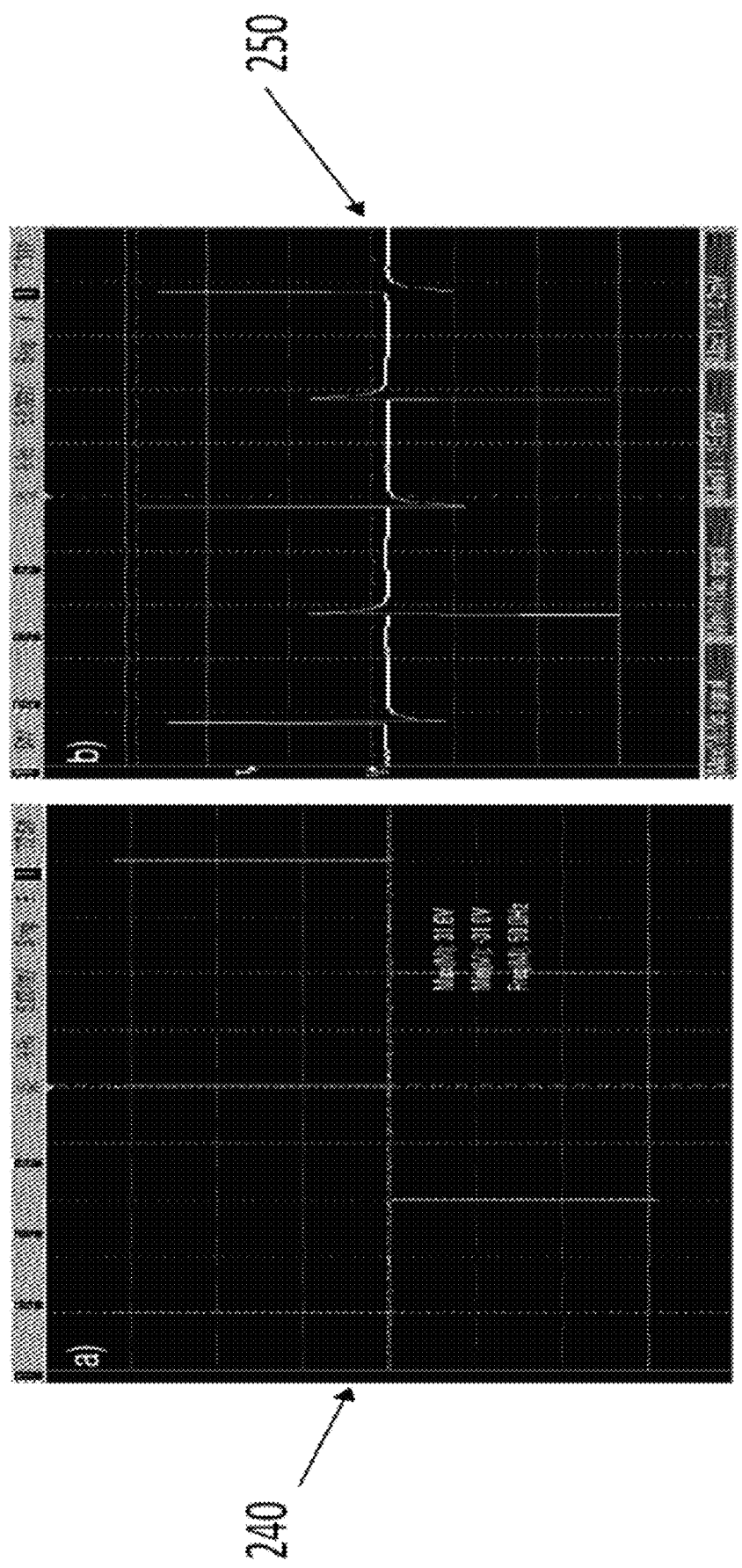

FIG. 16 illustrates (on the left) a biphasic rectangular pulse 240 generated by the improved pulse generator 220 and (on the right) the resulting waveform 250 received by the improved serpentine stimulus coil 200 of the present invention.

Figure 17:
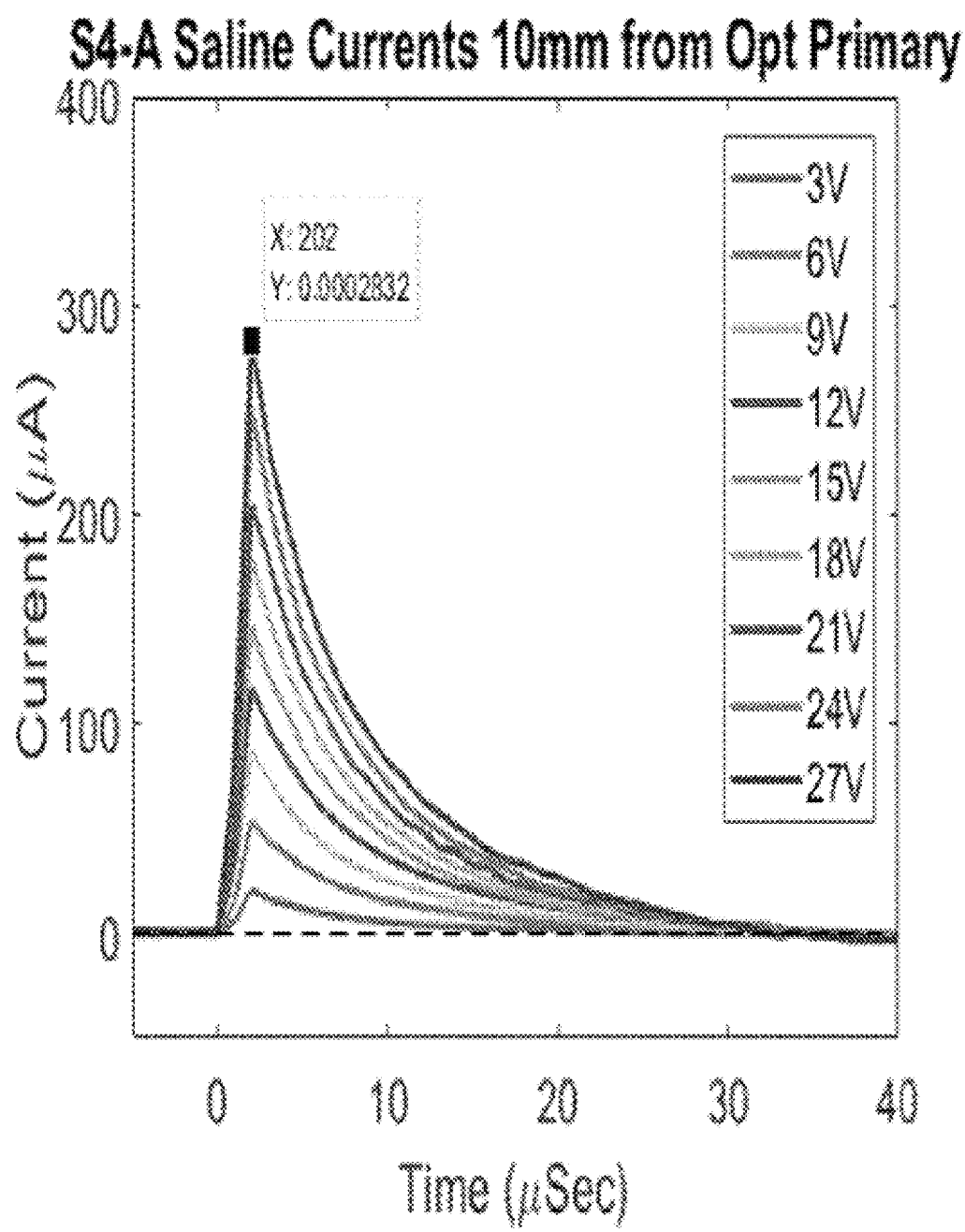
Figure 18:
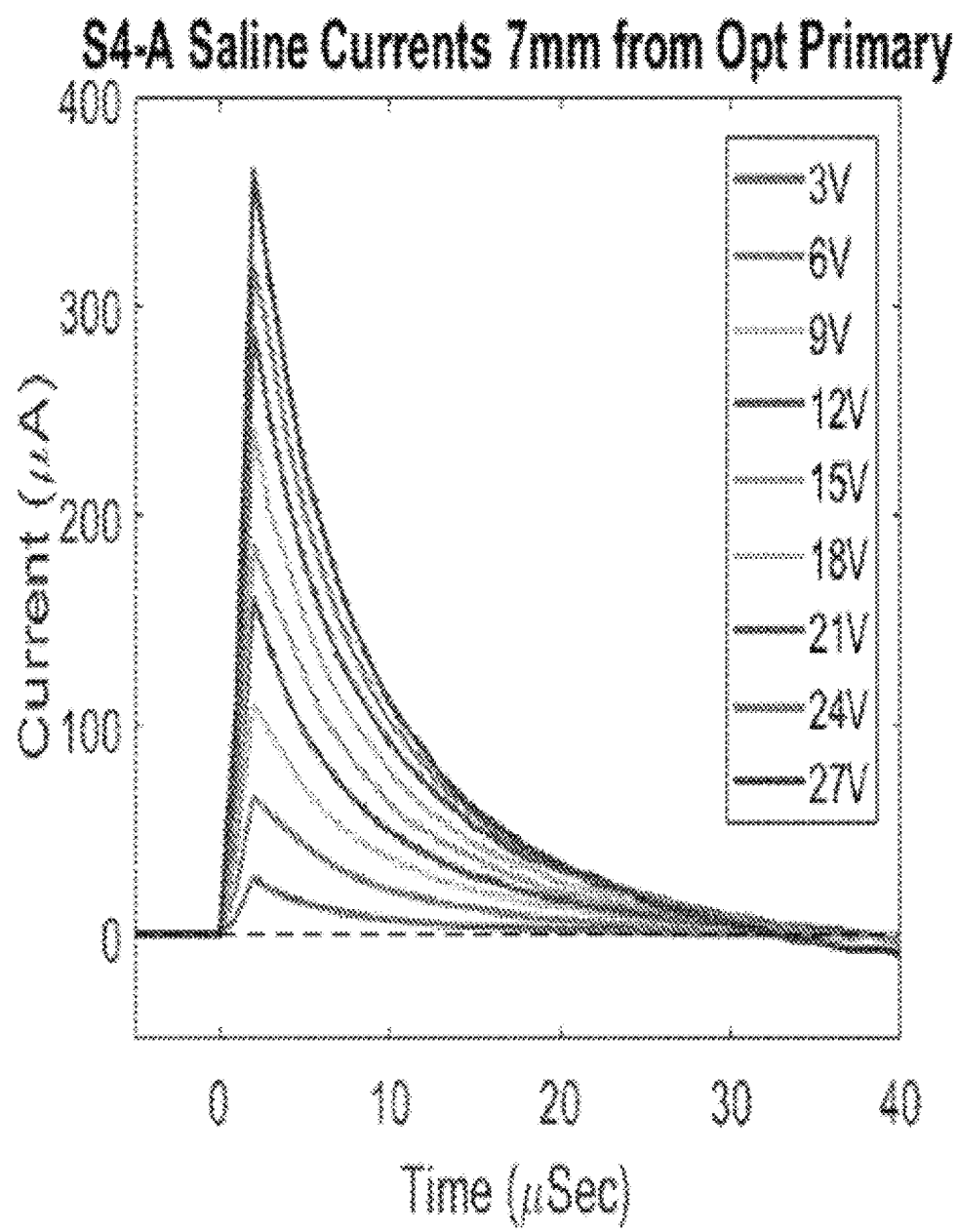
Figure 19:
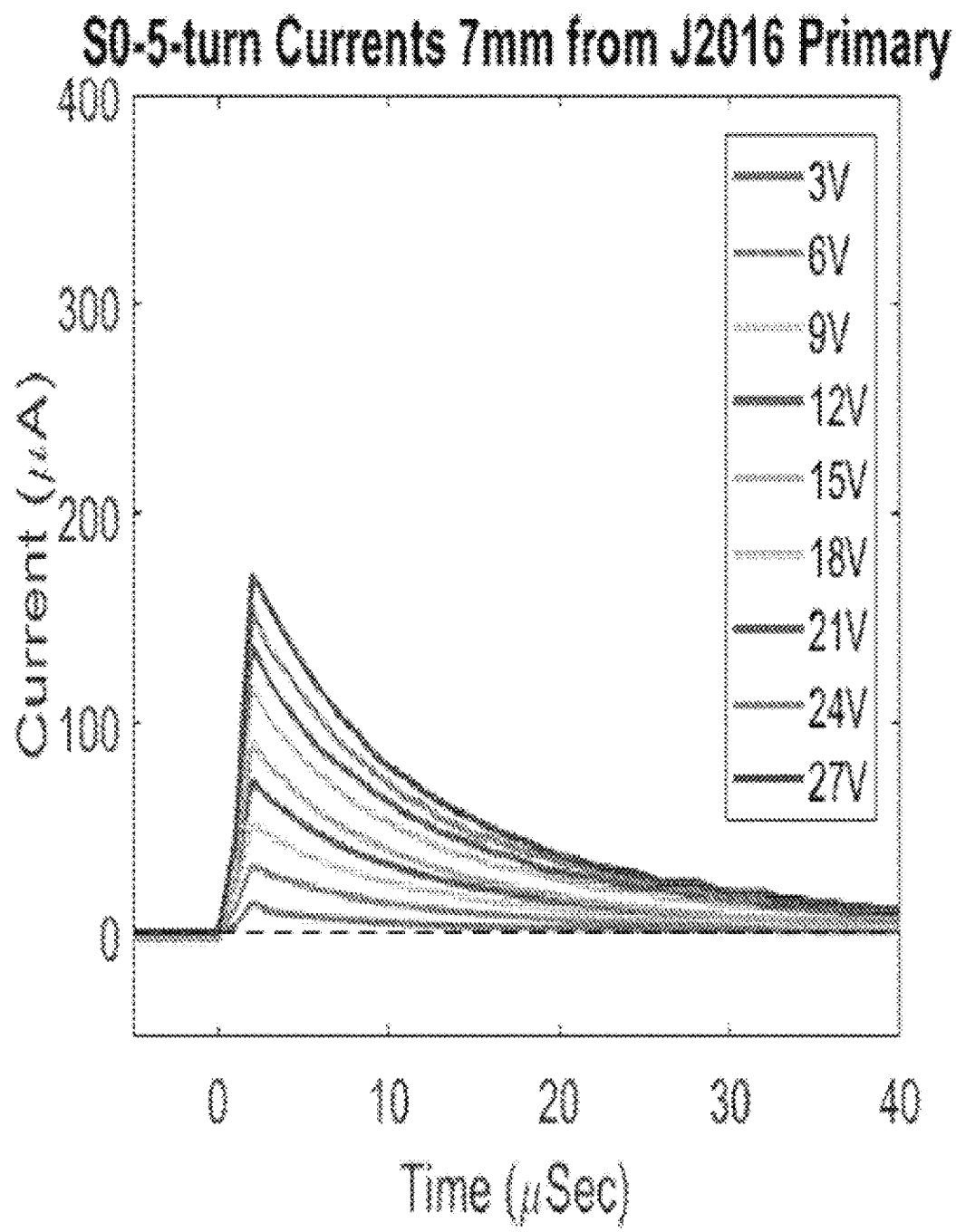

FIGS. 17-19 are charts illustrating the improvements generated through the use of the improved pulse generator 220 of the present invention over a range of voltages by comparing the currents measured at the primary coil resulting from the use of the improved pulse generator 200 (FIG. 18) to the currents measured at the primary coil resulting from the use of the prior pulse generator (FIG. 19).

Like reference, numbers and designations in the various drawings indicate like elements.

DETAILED DESCRIPTION

The present invention is an improved stimulus coil for use with a wireless power transfer (WPT) system adapted to wirelessly administer energy to an eye of a mammalian subject for the purpose of reducing elevated intraocular pressure (IOP) for those experiencing glaucoma or pre-glaucoma ocular hypertension. This reduction in IOP is based on the delivery of time-varying electromagnetic fields to the eye in a therapeutically effective amount sufficient to (1) decrease the inflow of aqueous humor into the anterior segment of the eye (so-called "fluid inflow decrease") and/or (2) increase the outflow of aqueous humor from the anterior segment of the eye (so-called "fluid outflow increase"). As used herein, the "anterior segment" of the eye is the front third of the eye that includes the structures in front of the vitreous humor: namely the cornea, the iris, the ciliary body, and the intraocular lens. There are two fluid-filled spaces within the anterior segment of the eye: the anterior chamber and the posterior chamber. The anterior chamber of the anterior segment exists between the posterior surface of the cornea (i.e. the corneal epithelium) and the iris. The posterior chamber of the anterior segment extends between the iris and the suspensory ligament of the lens. Aqueous humor fills the spaces of the anterior chamber and posterior chamber to, among other things, provide nutrients to the surrounding structures. The wireless administration of energy to reduce IOP may take multiple forms, as will be described below.

Figure 1:
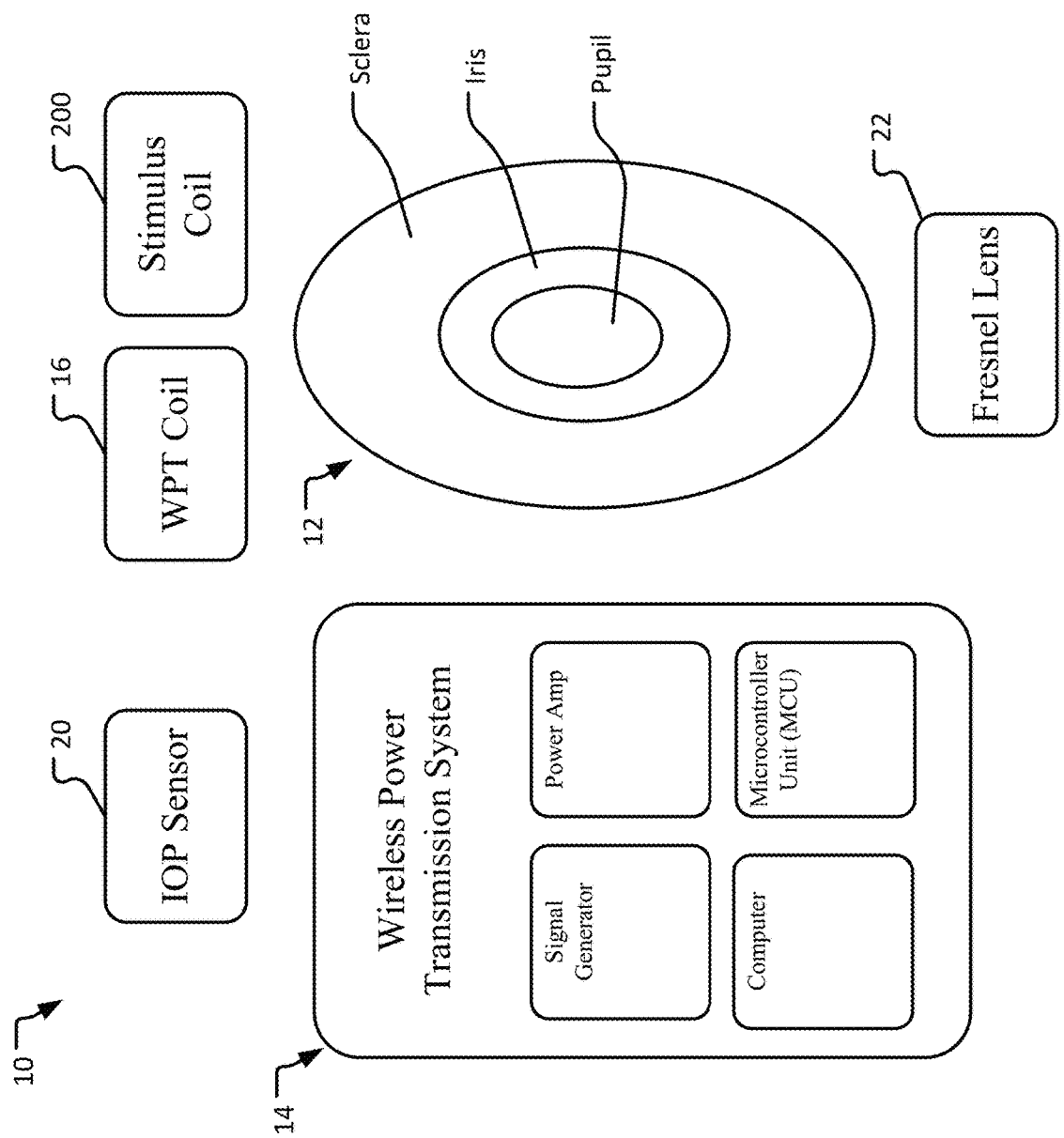
FIG. 1 shows a diagram of an example of a wireless glaucoma therapy system for use with the improved stimulus coil of the present disclosure.

FIG. 1 is a block diagram of a wireless glaucoma therapy system 10 for delivering a time-varying electromagnetic field to an eye 12 of a mammalian subject in conjunction with an improved stimulus coil according to the principles and techniques disclosed herein. To do so, the wireless glaucoma therapy system 10 includes a wireless power transfer (WPT) system 14 having suitable control and driving circuitry (e.g., a signal generator, a power amp, a microcontroller unit, a computer) for generating a time-varying electromagnetic field from a WPT coil 16 positioned and configured to deliver the time-varying electromagnetic field to the eye 12 via an improved stimulus coil 18 disposed on, within, or near the eye 12 of the mammalian subject. The WPT system 14 and the WPT coil 16 may be communicatively linked in any number of suitable manners, including a hard-wired connection (e.g. cable) as well as via wireless communication technologies.

The WPT coil 16 may be positioned near the eye 12 in any number of suitable manners, including, but not limited to, devices to enable the administration of wireless glaucoma therapy during normal activities of daily living (e.g., WPT coil 16 on eye-glasses), devices to enable the administration of wireless glaucoma therapy in a clinical setting (e.g., WPT coil 16 on an optical frame used by ophthalmologists and/or optometrists), and devices to enable the administration of wireless glaucoma therapy while the subject is sleeping (e.g., WPT 16 as part of a sleep mask, pillow, etc.). In each case, the WPT coil 16 delivers the time-varying electromagnetic field to the eye 12 via the stimulus coil 18 in a therapeutically effective amount to reduce the IOP within the eye 12 by decreasing the inflow and/or increasing the outflow of aqueous humor into and out of, respectively, the anterior segment of the eye 12.

The stimulus coil 18 is disposed in generally close proximity with the eye 12 so as to be able to deliver energy into the eye 12 in a therapeutically effective amount to accomplish the IOP reduction according to the principles set forth herein. More specifically, the stimulus coil 18 is configured to receive the electromagnetic field generated by the WPT coil 16 and transmit that energy directly into the eye 12. To facilitate this, the stimulus coil 18 may be positioned in any number of suitable physical locations relative to the eye 12, including (but not necessarily limited to) against the surface of the eye 12, near the surface of the eye 12 (e.g., such as by being embedded within a contact lens) and surgically implanted within any number of suitable structures and locations inside the eye 12 (e.g., intraocular lens (IOL), sub-conjunctival region, etc.). The physical location of the stimulus coil 18 on, near or within the eye 12 provides a higher level of energy transmission into the eye 12, which may result in IOP reduction in a shorter time period or to a greater extent than that accomplished by the WPT system 14 and WPT coil 16 alone.

The stimulus coil 18 may be used with any number of adjunctive technologies, including but not limited to a wireless IOP sensor 20 capable of monitoring the intraocular pressure (IOP) within the eye 12 and/or a Fresnel lens 22 to focus incoming light rays onto the retina of the eye 102 for the purpose of vision correction.

The wireless IOP sensor 20 may be implantable within the eye 12 and communicatively linked with the WPT system 14 to regulate or modify the delivery of therapy in a closed-loop manner based on the values of the monitored IOP. The closed-loop control of the WPT system 14 (including WPT coil 16 and the stimulus coil 18) may be accomplished in any suitable manner, including, but not limited to, the use of executable software on the computer and/or an "app" on a smartphone, tablet, etc., to modify the delivery of the wireless glaucoma therapy based on the measured IOP in the eye 12.

The Fresnel lens 22 may be constructed with a series of metallic traces in order to establish a given optical power to achieve vision correction, namely, by focusing light passing through the Fresnel lens 22 on the retina of the eye 12. The metallic traces of the Fresnel lens 22 may also be capable of receiving the time-varying electromagnetic fields and delivering that energy to the eye for the purpose of glaucoma therapy, especially if the Fresnel lens 22 is electrically coupled to the stimulus coil 18 according to one embodiment of the present disclosure. The Fresnel lens 22 may be employed with the WPT system 14 (including WPT coil 16) in order to deliver glaucoma therapy in addition to vision correction.

Figure 2:
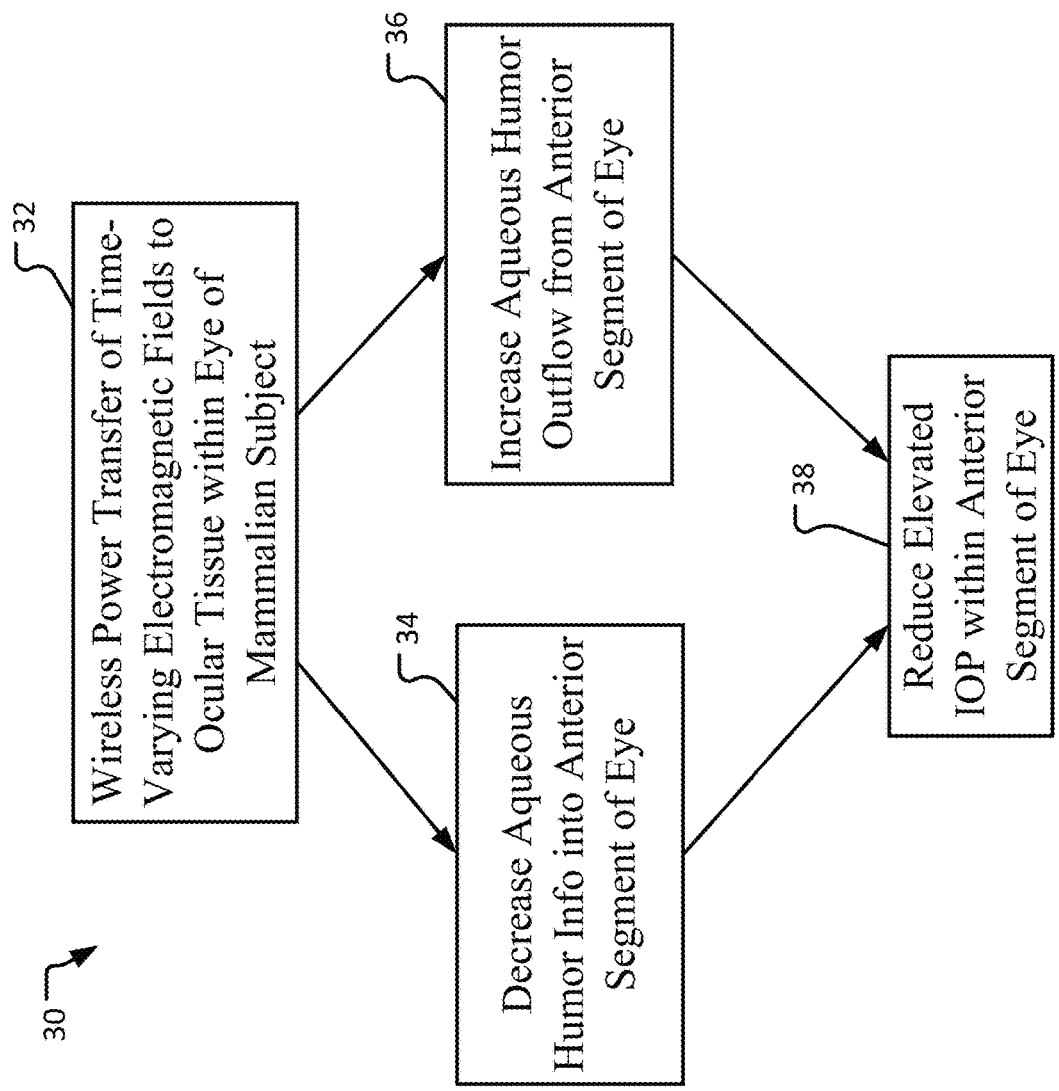
FIG. 2 shows the fundamental methodology of the wireless glaucoma therapy system.

FIG. 2 shows the fundamental methodology 30 of the wireless glaucoma therapy system (e.g., the system 10 shown in FIG. 1). Step 32 involves wirelessly transmitting power in the form of time-varying electromagnetic fields to ocular tissue with an eye of a mammalian subject (e.g., eye 12 shown in FIG. 1). Depending upon the manner of wireless power transfer, the wireless transmission of power (step 32) will result in a decrease in aqueous humor inflow into the anterior segment of the eye (step 34) and/or an increase in aqueous humor outflow from the anterior segment of the eye (step 36). More specifically, the wireless transmission of energy via WPT coil (e.g., WPT coil 16 of FIG. 1) and stimulus coil (e.g., stimulus coil 18 of FIG. 1) may provide both a decrease in the aqueous humor into the anterior segment of the eye (step 34) and an increase in the aqueous humor outflow from the anterior chamber of the eye (e.g., eye 12), thus reducing an elevated IOP within the anterior segment of the eye (38).

Figure 3:
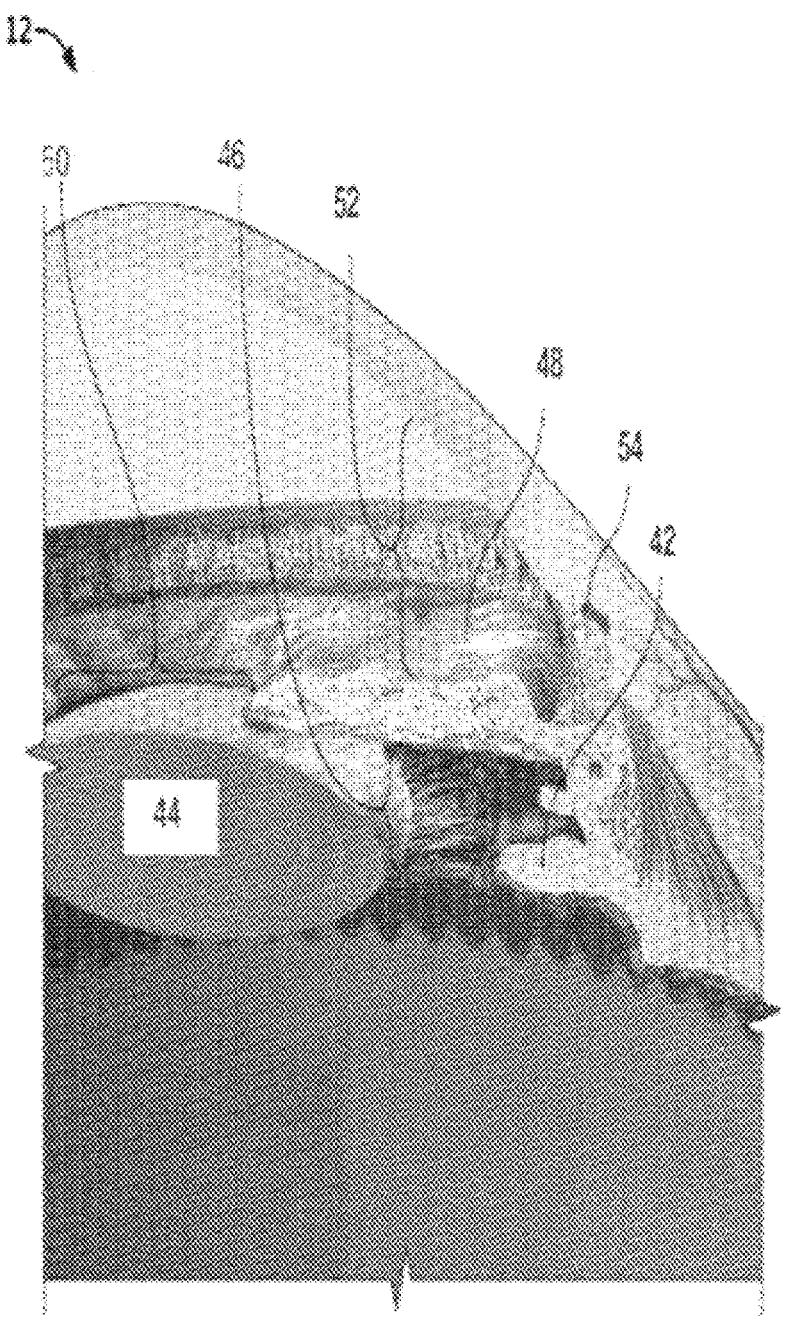
FIG. 3 shows a diagram of the relevant anatomy of an eye of a mammalian subject.

FIG. 3 shows a diagram of the relevant anatomy of the eye 12 of a mammalian subject, specifically in this figure, a human. Within the eye 12, the ciliary body 42 includes a smooth-muscle tissue called the ciliary muscle, which has two different orientations of muscle (circular and longitudinal) with separate functions. The circular muscle tissue of the ciliary body 42 controls the shape of the lens 44 in the eye 12, which changes the focus of the eye 12 so that the image will be clear on the back of the retina. The longitudinal muscle tissue of the ciliary body 42 controls the configuration of the trabecular meshwork. The aqueous humor is secreted by the ciliary body 42.

Aqueous humor is secreted into the posterior chamber 46 of the anterior segment of the eye 12 between the iris 48 and lens 44. It washes over the lens 44 and then moves through the pupil 50 into the anterior chamber 52 of the anterior segment. Ultimately, much of the aqueous humor leaves the eye 12 through two primary pathways, namely a pathway through as least part of the Canal of Schlemm 54 and an uveoscleral pathway through at least part of the ciliary body and choroid. Aqueous humor production, flow and drainage are important for nourishing the front of the eye 12, removing metabolites and normal vision.

In a patient with glaucoma, the aqueous humor builds up in the eye 12. This can be due to the blocking or a slowing of the drainage of the aqueous humor in the trabecular meshwork. As the excess fluid builds in the eye 12, it increases the intraocular pressure. As this pressure increases, it causes the optic nerve to get damaged. If left untreated, the pressure does so much damage to the optic nerve that it can eventually lead to blindness.

Figure 4:
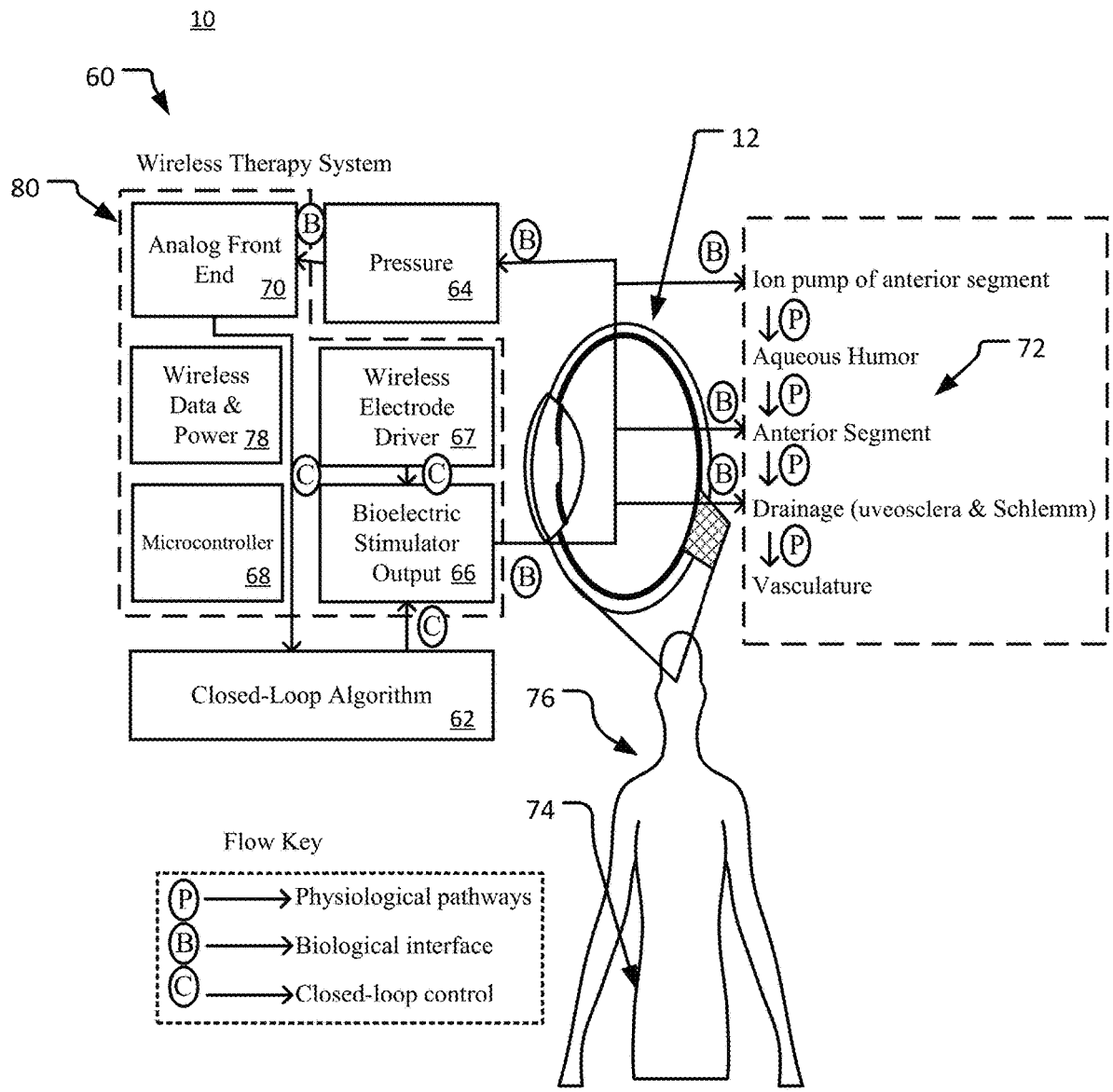
FIG. 4 shows a block diagram of an example of a closed-loop wireless glaucoma therapy system, including various components and the resulting biological effects.

FIG. 4 shows a block diagram of an example of the glaucoma therapy system 10 in a closed-loop wireless embodiment, including various components and the resulting biological effects. The wireless glaucoma therapy system 10 includes a controller system 60 (in dashed lines) with various components and circuitry to effectuate a closed-loop algorithm 62 for the monitoring and adjusting the glaucoma therapy based on feedback provided by a wireless pressure sensor 64 (e.g., IOP sensor 20 in FIG. 1) implanted within the eye 12 of the patient.

More specifically, the stimulator output 66 (driven by the wireless electrode driver 67) will transmit a given time-varying electromagnetic field into the eye 12 (via WPT coil 16 and stimulus coil 18) depending upon any number of input parameters and/or instructions being acted upon by the microcontroller 68 (e.g., input from the wireless IOP sensor 64 via the analog front end 70). By operating in a closed-loop manner, the wireless glaucoma therapy system 10 can dynamically influence the various physiological pathways 72 to achieve a desired decrease in aqueous humor inflow into and/or increase in aqueous humor outflow from the anterior segment of the eye 12.

In one embodiment, the wireless glaucoma therapy system 10 may be programmed and/or controlled by the patient and/or a physician via a mobile device 74 (e.g., iPhone by Apple, Inc., Galaxy by Samsung, Inc., iWatch by Apple, Inc., etc.) with software capable of wirelessly controlling the function of certain (or all) components of the wireless glaucoma therapy system 10. For example, it is contemplated that the components of the controller system 60 may be disposed on or within the various devices for positioning a WPT coil 16 in proximity to the eye 12 of the subject 76 (e.g. glasses, optical frames, sleep mask, pillow). In this case, the mobile device 74 could be used to wirelessly control the operation of the controller system 60, such as via Bluetooth connectivity between the mobile device 74 and the controller system 60.

The controller system 60 can include components to provide wireless data and power (78) that permits the control device 80 to wirelessly output data to a base station (separate from the mobile device 74) and to be wirelessly powered and/or charged. This output data can include a variety of different patient data, such as a log of conditions detected and therapies delivered, alerts as to currently detected conditions (e.g., elevated IOP), and/or other data. The controller system 60 can transmit this data wirelessly. The controller system 60 can be powered wirelessly (e.g., via RF signals) and can additionally include a local power source (e.g., battery) that can be charge via the wireless signals and that can power the controller system 60 when the wireless signal is unavailable.

The controller system 60 includes an analog front end 70 that receives wireless signals transmitted by the wireless IOP sensor 64. The analog front end 70 provides the received signals to the signal processing subsystem of the microcontroller 68. Signal processing can be performed onboard or offboard, and can involve using a closed-loop algorithm 62, which can be used to identify particular physiological conditions within the patient 76 and can determine, based on the particular detected conditions, whether to modify or alter the bioelectric stimulation at one or more WPT coils located in proximity to the eye 12 and one or more stimulus coils disposed on or within the eye 12.

The closed-loop algorithm 62 can use any of a variety of appropriate techniques to learn the particular physiology of the patient 76 and the patient's particular response to therapy, and can use that information to determine when, how, and under what conditions to provide therapy for the patient 76. For example, the closed-loop algorithm 62 can be initially calibrated for the patient by a physician or other trained technician in a clinical setting, which can involve providing various stimulations and recording the physiological response of the patient 76. After being initially calibrated, the closed-loop algorithm 62 can continue to learn and adapt over time by analyzing data generated by the wireless IOP sensor 64, therapy provided to the patient 76, and the patient's response to the therapy. The closed-loop algorithm 62 can repeatedly monitor patient data and apply stimulation to the ion pump and/or eye muscles (e.g., eye muscles affecting eye drainage) when appropriate until the patient's elevated IOP condition has been reduced and/or dropped below a threshold level. The closed-loop algorithm 62 can be automatically implemented without explicit patient direction.

Figure 5:
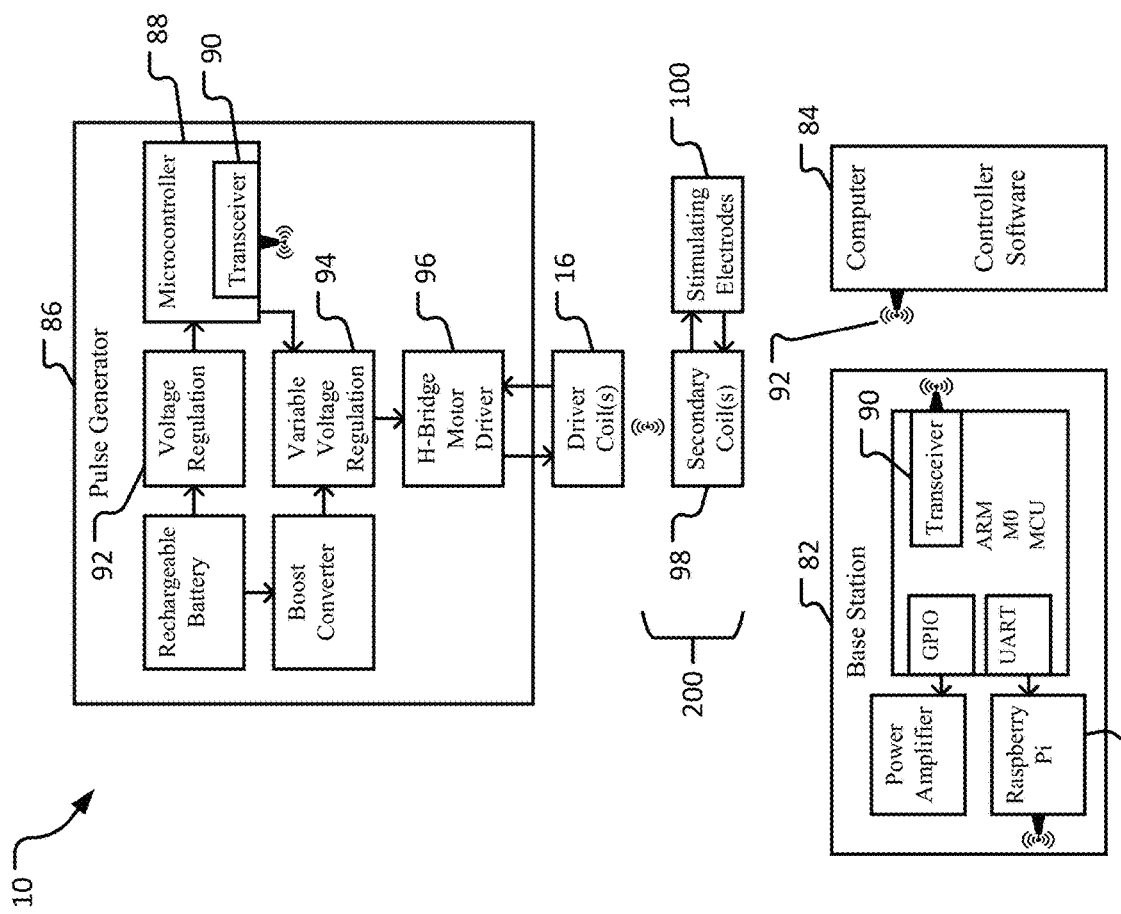
FIG. 5 shows an example of the wireless power transfer (WPT) system of the wireless glaucoma therapy system, including a base station and a signal generator.

FIG. 5 shows an example of the glaucoma therapy system 10 in an open-loop wireless embodiment, including various components. The wireless glaucoma therapy system 10 includes a base station 82, a computer 84, and a pulse generator 86. The base station 82 and computer 84 cooperate to wirelessly transmit control signals to the pulse generator 86 to effectuate control programming set forth in software being executed by the computer 84. The base station 82 may be wirelessly connected to the pulse generator 86 via any suitable wireless communication technology or system (e.g., Raspberry Pi 95) capable of wirelessly communicating with a microcontroller 88 of the pulse generator 86. The base station 82 may also be wirelessly connected to the computer 84, using transceiver 90 and its associated antenna along with another transceiver and associated antenna 92 provided with the computer 84. It will be appreciated that, although shown with wireless communication between the base station 82 and the computer 84, as well as between the base station 82 and the pulse generator 86, any or all of these wireless communications pathways may be replaced via physical communications links (e.g. computer cable).

The pulse generator 86 receives the wireless control communications from the base station 82 via the transceiver 90 in communication with (or forming part of) the microcontroller 88. The microcontroller 88 cooperates with circuitry (e.g., voltage regulation 92, variable voltage regulation 94) to drive an H-bridge driver 96 coupled to one or more drive (WPT) coils 16 to transmit a time-varying electromagnetic field. This electromagnetic field may be administered to the eye 12 via drive (WPT) coils 16 positioned in proximity to the eye and via one or more secondary coils 98 (forming part of the stimulus coil 18) located on or within the eye 12. Through the principles of wireless electromagnetic energy (e.g., inductive, far-field RF, optical, etc.) coupling, the secondary coils 98 may be adapted to receive the time-varying electromagnetic field from the drive (WPT) coils 16 and transmit that energy into ocular structures of the eye via one or more stimulating electrodes 100 (forming part of the stimulus coil 18) disposed on or within the eye. Based on WPT in combination with secondary (stimulus) coils 98, the wireless glaucoma therapy system 10 is capable of administering a therapeutically effective amount of energy to achieve the desired reduction in aqueous humor inflow into and outflow from, respectively, the anterior segment of the eye.

Figure 6:
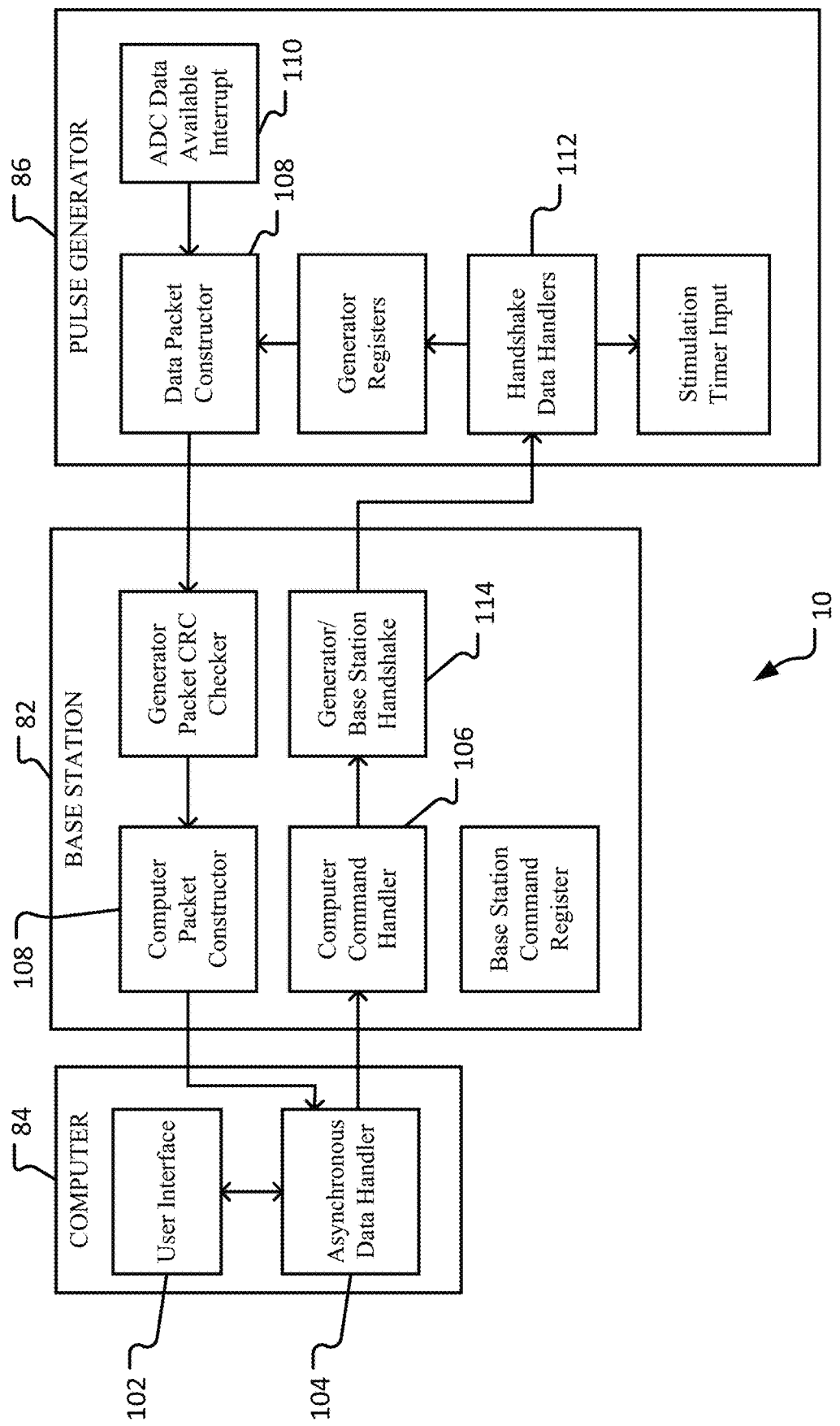
FIG. 6 shows a diagram depicting an example of the communication pathway of the wireless glaucoma therapy system.

FIG. 6 shows a diagram of depicting an example of the communication pathway between the components of the open-loop wireless glaucoma therapy system 10 of the type shown in FIG. 5, with base station 82, computer 84, and pulse generator 86. The communication within wireless glaucoma therapy system 10 starts on the left, with a user interfacing with the computer 84 such as inputting instructions or the like via User Interface 102 (e.g., keyboard, GUI, etc.). The computer 84 is communicatively linked with the base station 82 via an asynchronous data handler 104 that sends output signals to a computer command handler 106 and receives input signals from a computer packet constructor 108.

Bidirectional communication during use of the system can greatly increase the flexibility and possible application use of an implantable device such as the wireless IOP sensor described herein, which would be coupled to the analog-to-digital converter (ADC) Data Available Interrupt module 110. The ability to transmit data potentially removes the burden of on-board data storage from the implantable device, but it also allows the implantable device to communicate its current status and settings in real time, allowing for increased confidence in implant performance over time. Furthermore, the ability to receive data allows the implantable device to be configured, calibrated, and instructed before, during, and after implantation; increasing its adaptability to varying circumstances. An implantable device that can both receive and transmit data (such as the wireless IOP sensor) has the added benefit of allowing an external user or system to reactively send instructions to the implantable device based off of recorded data obtained by the implantable device; effectively creating a closed-loop system.

Bidirectional communication can be performed, as illustrated in FIG. 6, by enforcing a coordinated handshake protocol with a custom designed external base station 82 which facilitates all communications with any outside user. After the pulse generator 86 acquires a specific number of samples, for example 40 data samples, from its analog-to-digital converter (ADC) Data Available Interrupt 110, a microcontroller with the pulse generator 86 initiates a data-packet transmission to the base station 82 using an on-board radio. Data packets can be constructed, for instance using conventional packetization techniques, to include recoded data, and subsequently communicated via transmission signal from a data packet constructor 618.

After a successively transmitting multiple packets, for instance the 100th data packet, the pulse generator 86 initiates a hand-shake with the base station 82. The handshake can be performed between respective handshake units (112, 114). After transmitting a specified data packet, or a data packet otherwise deemed as the end of communication (e.g., 100th data packet), the pulse generator 86 sets its radio to receive mode, and listens for a data packet from the base station 82 for a time, typically not exceeding 10 milliseconds. This gives the base station 82 an opportunity to send a single data packet to the pulse generator 86. The data packet can contain a 45-byte long payload, which is used to set firmware registers in the microcontroller of the pulse generator 86 that stores data acquisition, stimulation, and communication settings.

In some cases, the handshake driven communication scheme allows the pulse generator 86 to transmit acquired data rapidly, while maintaining the ability to receive data from an outside source with minimal radio activation time. For example, given a total data acquisition sample frequency of 5 kHz, the radio of the pulse generator 86 will transmit 125 data packets per second and initiate a handshake once every 800 milliseconds. Given the radio on-time described above, bidirectional communication is achieved with the radio being deactivated at least 86.7% of the time.

Another challenge in a wireless communication scheme is increasing data robustness. In order to properly analyze any data recorded by the pulse generator 86, the ability to identify when data has been corrupted or lost may be desired. Data can be corrupted or lost during wireless transmission in various conditions, including: if it is obstructed by a blockage that can absorb RF energy; if a nearby device communicating on the same frequency creates interference; and if the distance between the pulse generator 86 and the base station 82 exceeds the transmission range of the pulse generator 86. Furthermore, data can be lost in the scenario if the pulse generator 86 suddenly loses power during data acquisition or transmission.

Figure 7:
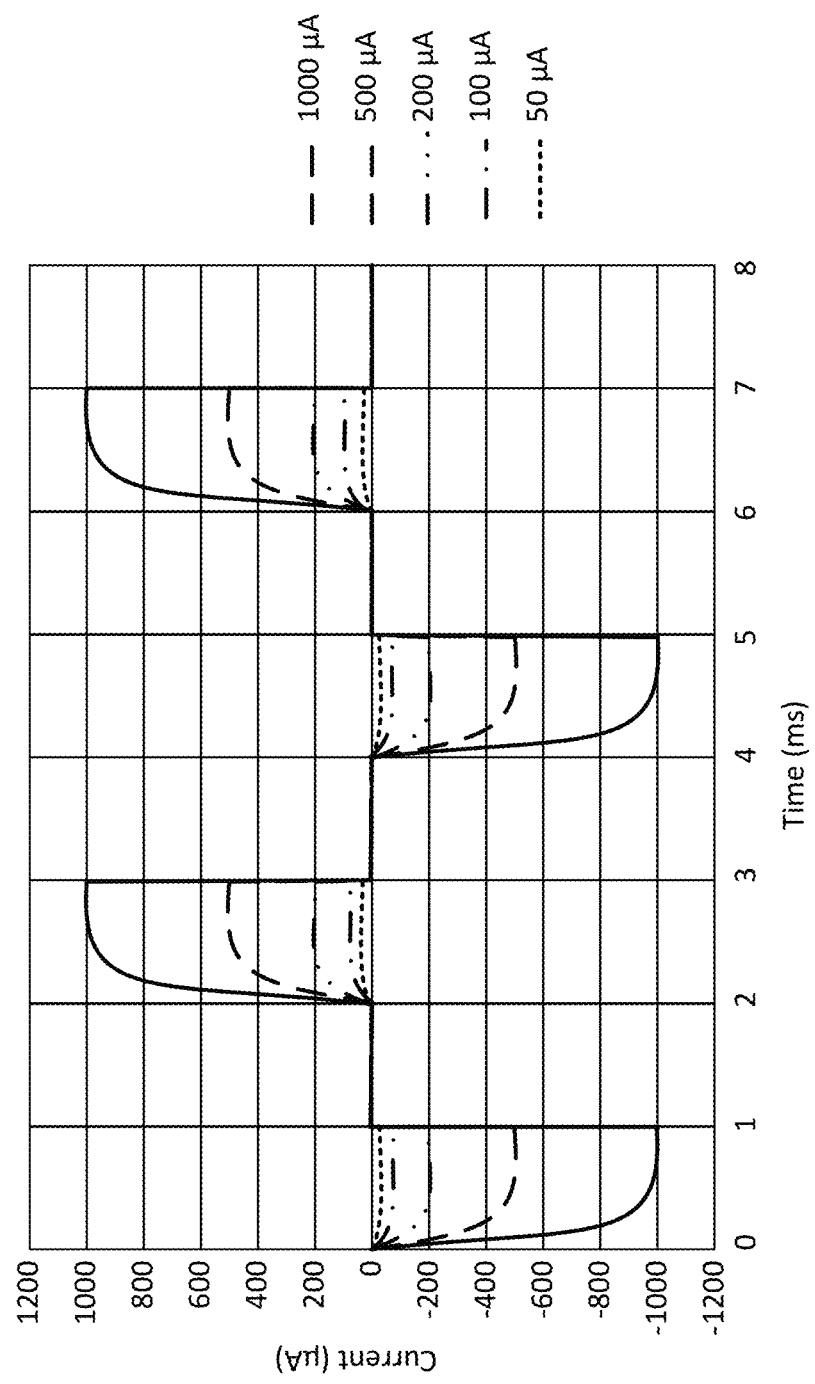
FIG. 7 shows an example graph displaying current-controlled, biphasic output measured from the stimulator outputs aspect of the wireless power transfer system.
Figure 8:
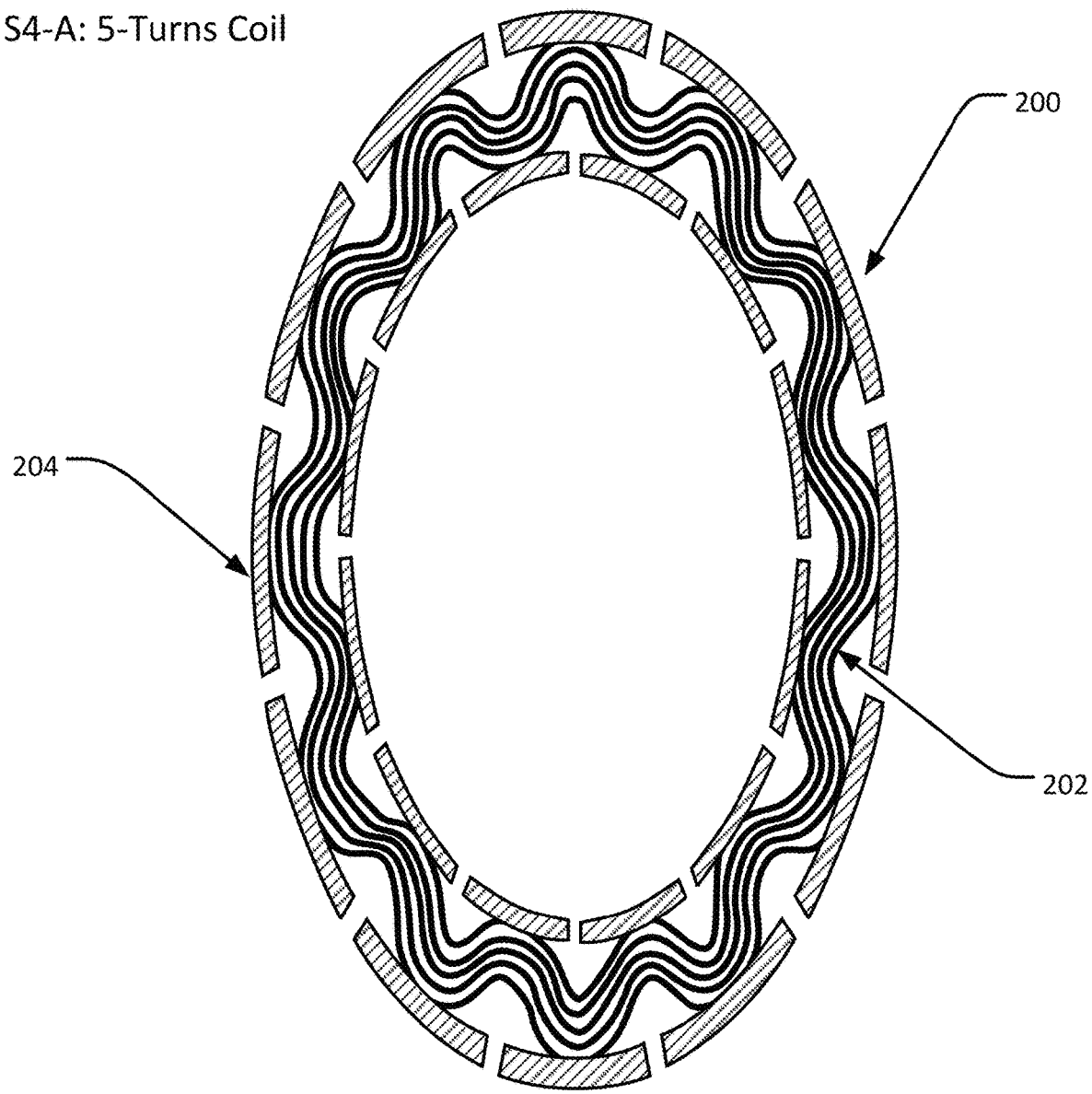
FIGS. 8-10 are top views of an improved stimulus coil of the present invention for implementing the disclosed techniques.
Figure 9:
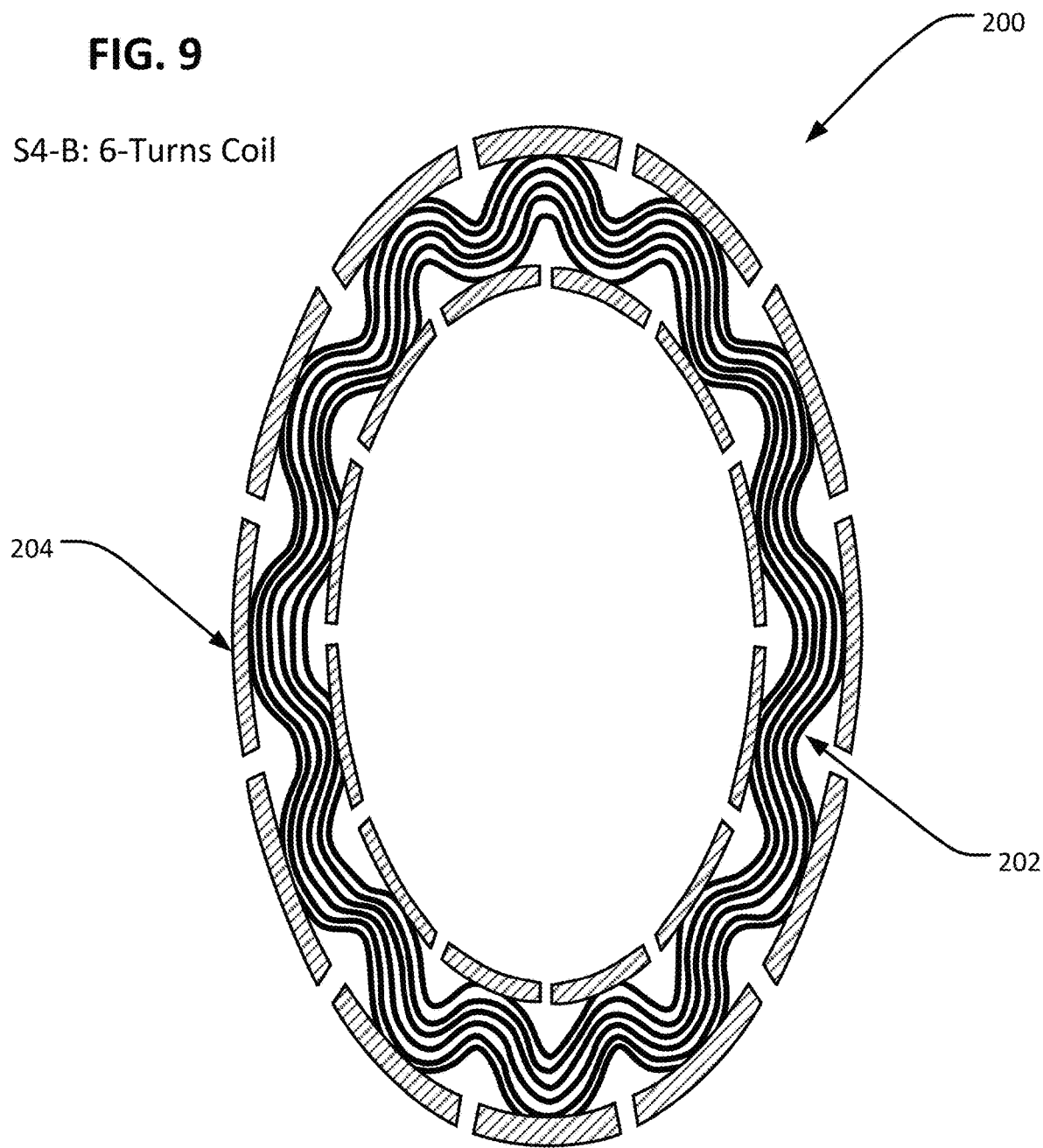
Figure 10:
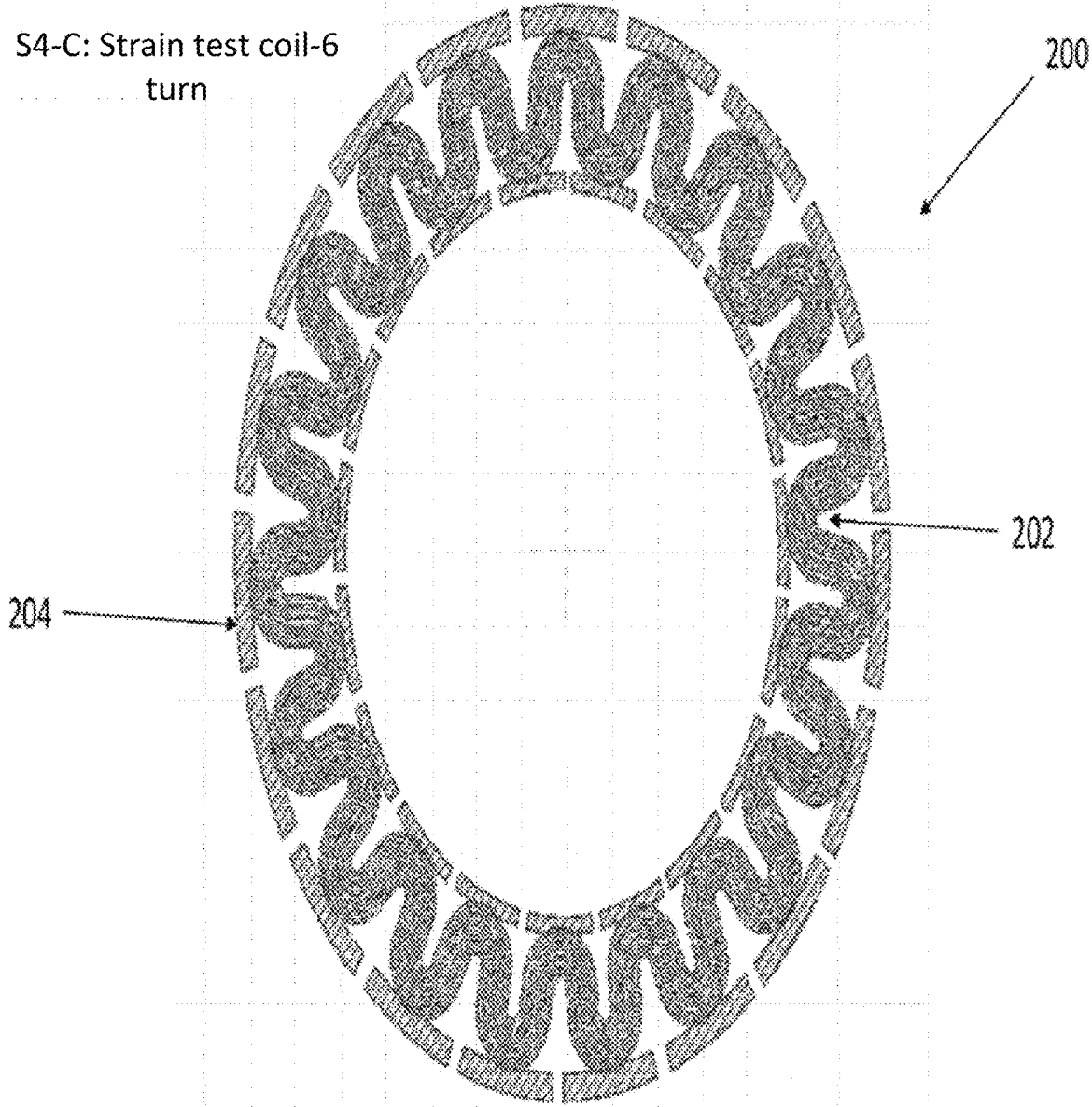

FIG. 7 shows a graph displaying an exemplary current-controlled, biphasic output signal 116 measured from the stimulator output of the wireless power transfer system 10 according to principles of the present disclosure. In this example, the stimulator output is measured on a benchtop using a 10 kΩ load across the stimulator outputs. The graph displays the output signal 116 as a relationship between time (ms), along the X-axis, versus current (μA) along the Y-axis. Pulse width, current amplitude, and duty cycle can be selectable parameters in real-time through reverse telemetry from the base station 82 to the WPT coil 16 or other suitable wirelessly powered device. A pulse width of 1 ms and a 50% duty cycle are used here to illustrate the current output for a range of amplitude settings.

FIGS. 8-11 are views of an improved stimulus coil 200 of the present invention. The stimulus coil 200 is an improvement when compared to the stimulus coils disclosed in commonly-owned and U.S. Provisional Patent App U.S. 62/584,691 filed Nov. 10, 2017 entitled "Stimulus Coil for Wireless Glaucoma Therapy," which is hereby incorporated in its entirety into this disclosure and attached hereto as Exhibit A (hereinafter "the '691 Provisional"). FIG. 12 shows the stimulus coils of the '691 Provisional (namely, the "round" stimulus coil 150, the "serpentine" stimulus coil 150, and the "serpentine plus" stimulus coil 18) next to the "improved serpentine" stimulus coil 200 of the present invention (sometimes referred to herein as the "S4 Coil").

There are four key parameters that influence the current amplitude on these stimulus coils when used with the wireless glaucoma therapy system 10, namely, tissue resistance (Rt), contact resistance (Rcon, which is the interfacial resistance between the contact pad and eye), internal resistance of the coil (Rcoil), and the magnetomotive force (MMF). As compared to the prior stimulus coils (round stimulus coil 150, serpentine stimulus coil 160, and serpentine plus stimulus coil 18), the improved serpentine stimulus coil 200 of the present invention encounters the same tissue resistance (Rt), has the same or slightly smaller contact resistance (Rcon), has increased internal coil resistance (Rcoil), and the same approximate electromotive force (MMF). The increased internal coil resistance (Rcoil) can be compensated via increased thickness of the gold used to make the stimulus coil 200.

The improved serpentine stimulus coil 200 has similar specifications as the round stimulus coil 150 in terms of its electric, magnetic, mechanic, and physiologic properties. The round stimulus coil 150 (sometimes referred to herein as "Coil S0") was shown to provide electric stimulation to effectively reduce the intraocular pressure (IOP) in mammalian patients suffering from heightened IOP. However, due to the mismatch between the 2D flat coil to 3D spherical surface on the eye, on occasion the patient may experience discomfort during the wearing of the round stimulus coil 150.

To solve this issue of discomfort, the inventors developed the serpentine stimulus coil 160 and serpentine plus stimulus coil 18 (Coils S2 and S3 in FIG. 11) of the '691 Provisional, which provided much better eye accommodation results. While an improvement over the round coil 150, the S2 and S3 coils where not able to produce radial current and similar current density as the round stimulus coil 150 (Coil S0). For the serpentine coil 160, the stimulation current direction is not on the radial direction and only a small portion of the current flows in the radial direction. This non-uniform current distribution is not able to provide enough current at desired levels to effectively stimulate the eye, and thus the results of reducing IOP from clinical trial were not as good as the round stimulus coil 150 (Coil S0).

In order to meet the electrical requirements (e.g., effective stimulation current amplitude and direction) and the mechanical requirements (e.g., comfortable accommodation on the surface of the eye), the inventors developed the improved serpentine stimulus coil 200 (Coil S4) of the present invention. The S4 Coil takes advantage of the merits of both the round stimulus coil 150 (Coil S0) and the serpentine stimulus coil 160 (Coil S2). The improved serpentine stimulus coil 200 (Coil S4) includes a serpentine pattern 202 as the main mechanical supporting structure for the best accommodation (similar to Coil S2) and a circle pattern 204 as the electric stimulation output port to provide the qualified stimulation current (similar to Coil S0). In some embodiments, stimulus coil 200 can include links extending between the various traces (also called turns) that allow stretching between the adjacent traces.

Figure 11:
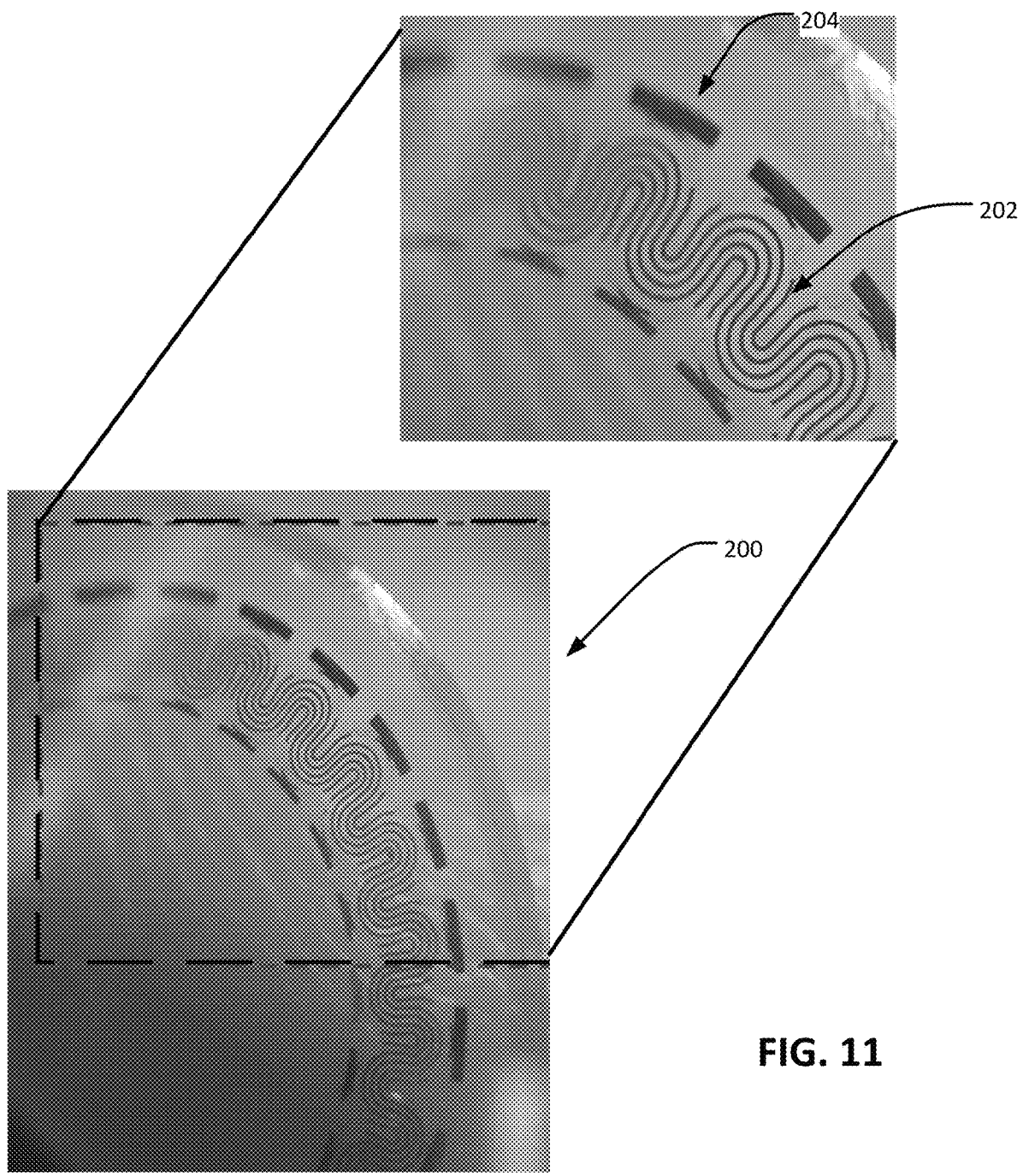
FIG. 11 shows a perspective view and an exploded view of another large serpentine stimulus coil for implementing the disclosed techniques.
Figure 12:
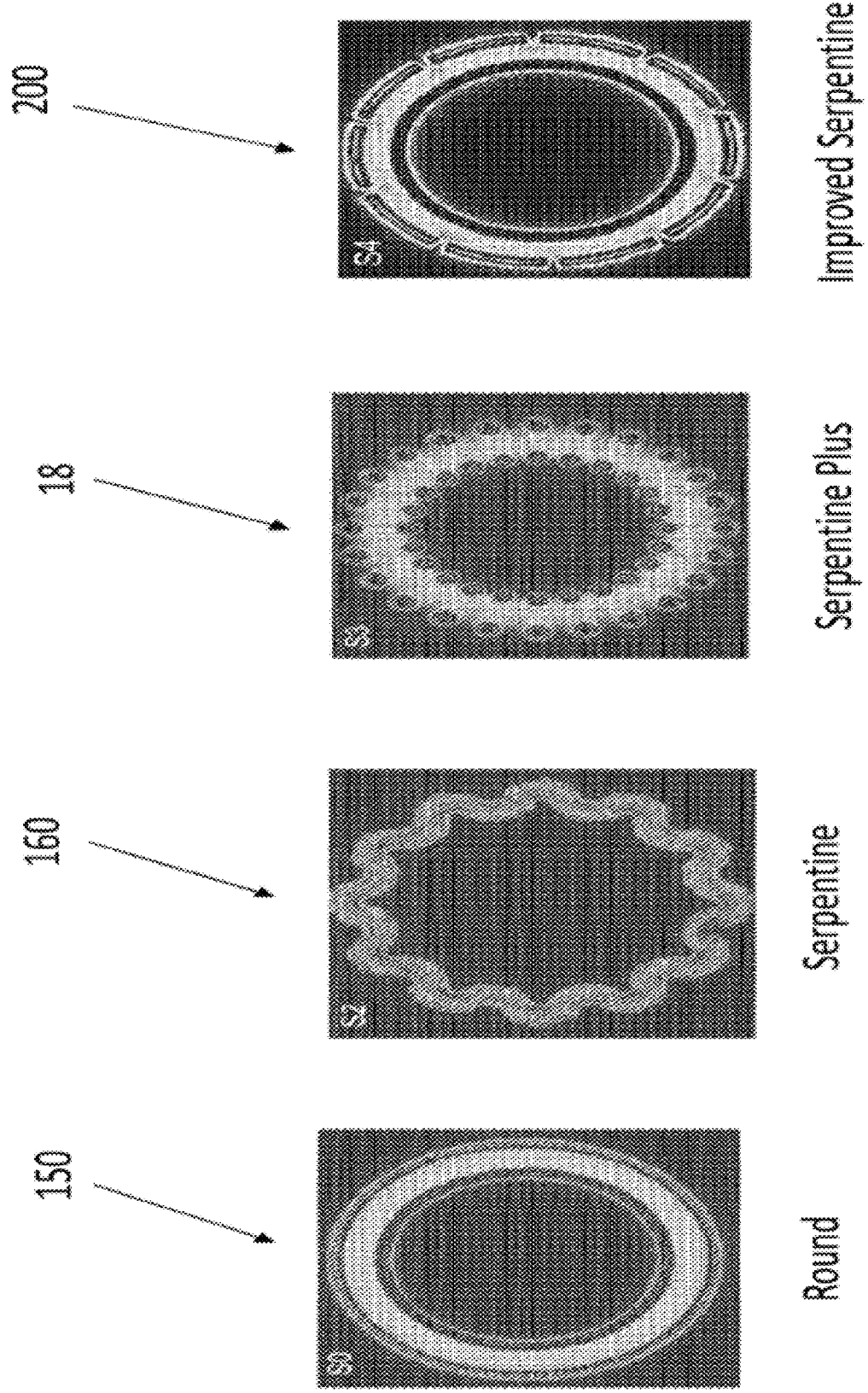
FIG. 12 shows the current density of the improved stimulus coil of the present invention (Coil S4, far right) relative to the current densities of prior stimulus coil designs by the inventors of the present invention, including a "round" stimulus coil 150 (Coil S0, far left), a "serpentine" stimulus coil 160 (Coil S2, second from left) and "serpentine plus" 18 (Coil S3, second from right).

With reference to FIG. 11, the stimulus coil takes the form of a serpentine stimulus coil 202 formed into multiple traces (e.g., 4, 5 or 6 traces, also called turns) disposed in a generally serpentine manner. In the embodiment shown in FIG. 11, the serpentine stimulus coil 202 includes four traces. The outermost trace and the innermost trace abut electrodes 204. In some embodiments, the outermost and innermost traces can be discontinuous, as shown in FIG. 11, with multiple smaller serpentine curves connecting portions of the traces that abut the electrodes 204 to portions of the trace that are spaced away from the electrodes 204. Such a configuration can aid in accommodating the curvature of the eye. The electrodes 204 may be of any desired length and are generally rectangular in shape. Accordingly, the electrodes create a generally circular pattern for electrical stimulation. The serpentine structure advantageously allows the stimulus coil 200 to accommodate the curvature of the eye and the tightness of the coils can alter the allowable curvature.

The electric simulation results of all four types of coils is shown in FIG. 12, illustrating the current distribution of the round stimulation coil 150, the serpentine stimulus coil 160, the serpentine plus stimulus coil 18 and the improved serpentine stimulus coil 200 (Coils S0, S2, S3 and S4, respectively). The color plots represent the amplitude of the current density, red and blue means maximum and minimum, respectively. A review of FIG. 12 reveals that the current in the round stimulus coil 150, the serpentine plus stimulus coil 18 and the improved serpentine stimulus coil 200 of the present invention (Coils S0, S3 and S4 respectively) follows the radial direction, but the current direction of the serpentine coil 160 (Coil S2) is scattered and non-uniform. The improved serpentine stimulus coil 200 (Coil S4) of the preset invention demonstrates most similar results as the round stimulus coil 150 (Coil S0) in the aspect of the current amplitude and direction. Based on this, the improved serpentine stimulus coil 200 (Coil S4) should be able to show similar performance on the IOP reducing, and more importantly provides best accommodation on eye for the comfort of patient.

Figure 13:
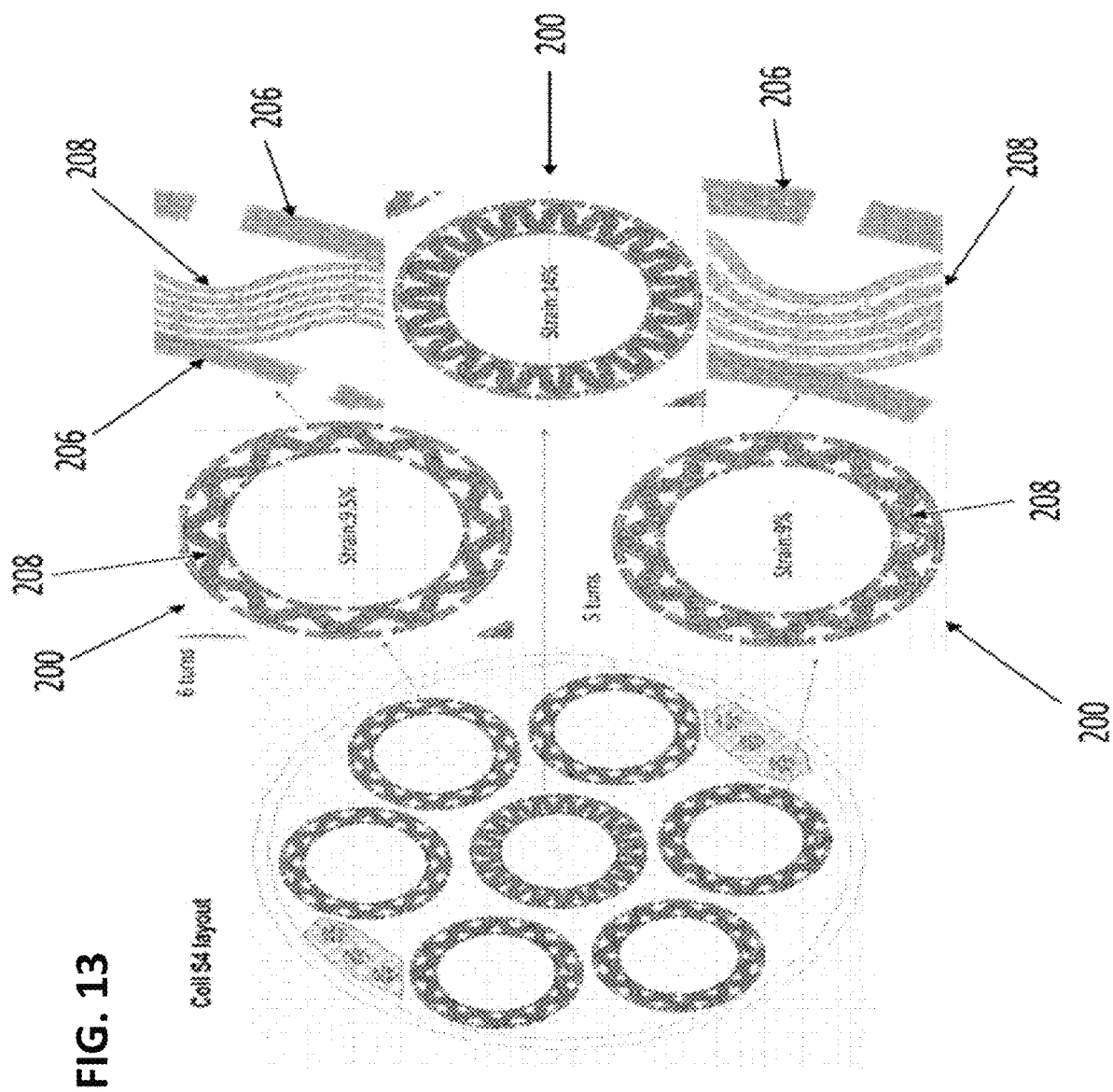
FIG. 13 is a coil layout of the entire wafer pattern employed during the manufacture of the improved stimulus coil of the present invention, illustrating the key features and resulting strain ability.

FIG. 13 illustrates a layout of the entire wafer pattern of the improved serpentine stimulus coil 200 (Coil S4) of the present invention. The light blue section 206 represents the open window area of the electrode as the output to provide stimulation current, and the red serpentine trace 208 in between makes the coil 200 fit on the eye surface well with strain ability from 9.5%-14%.

Figure 14:
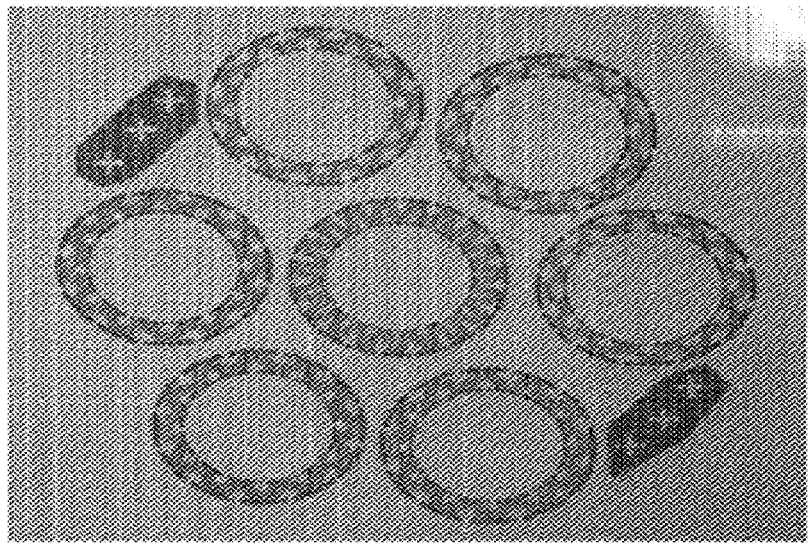
FIG. 14 illustrates three masks suitable for fabricating the improved serpentine stimulus coil 200 (Coil S4) with material Cr/IrO2 according to the present invention.
Figure 14:
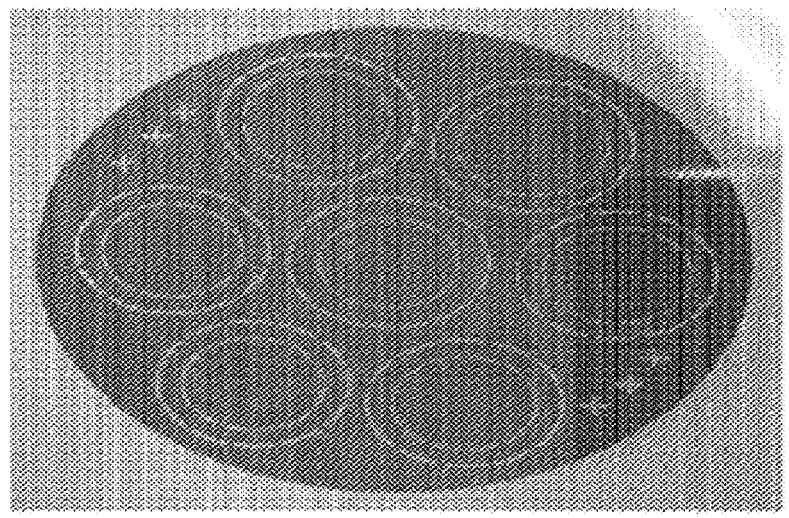
Figure 14:
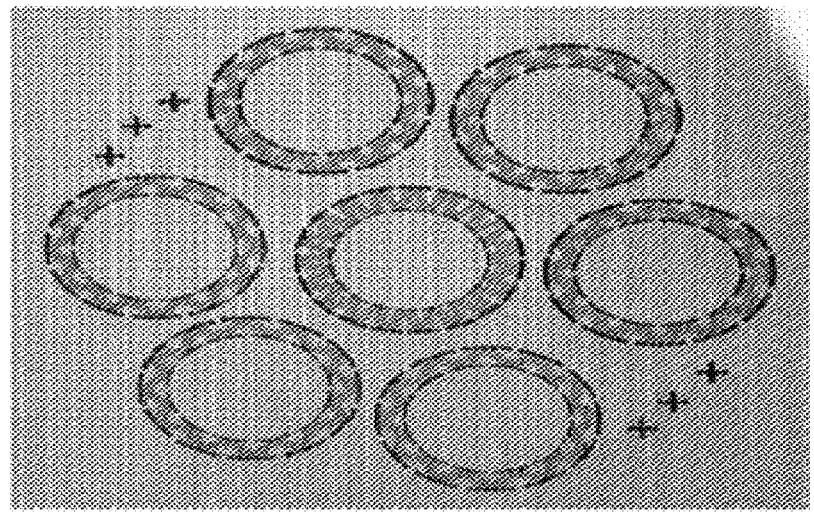

FIG. 14 illustrates three masks suitable for fabricating the improved serpentine stimulus coil 200 (Coil S4) with material Cr/IrO2. The first mask (on left in FIG. 14) will be used to build the gold electrode. The second mask (in the middle in FIG. 14) is designed to create the open window for electric contact with eye. The third mask (on the right in FIG. 14) will be used to etch the parylene to produce the entire outline of the coil 200. Photolithography technology will be applied during the entire fabrication process.

The improved serpentine stimulus coil 200 may form part of a contact lens (in the same manner shown in FIG. 18 of the '691 Provisional) and/or may be surgically implanted within the eye of a patient (in the same manner shown in FIG. 19 of the '691 Provisional). The descriptions set forth in the '691 Provisional with respect to these two implementations (namely, contact lens and implantation) apply equally to the improved serpentine stimulus coil 200 of the present invention and thus need not be repeated here.

Figure 15:
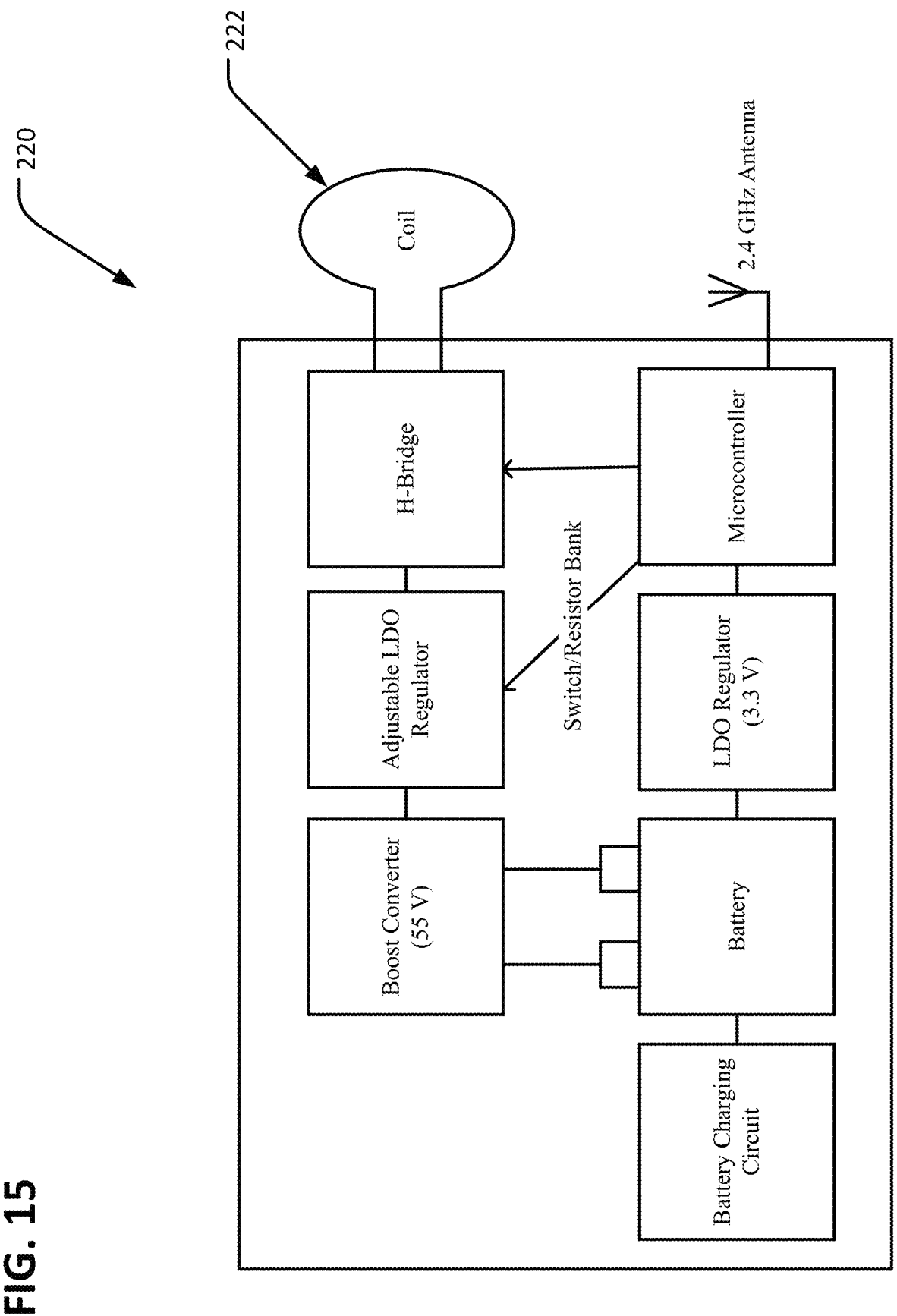
FIG. 15 is a block diagram of an improved pulse generator of the present invention for use in wireless glaucoma therapy according to the present invention.

FIG. 15 sets forth an improved WPT pulse generator 220 for use in the WPT system 14. The pulse generator circuit in the '691 Provisional was limited to a maximum voltage headroom of 27 V, which limited the amount of current capable of being delivered to the eye. When this prior pulse generator of the '691 Application was used with the round coil 150, a stimulation current of 30 µA was capable of being delivered to the eye. When applied to the serpentine stimulus coil 160 and the serpentine plus coil 18, however, the prior pulse generator was unable to meet this stimulation requirement of delivering at stimulation current of 30 µA into the patient's eye. The improved pulse generator 220 shown in FIG. 15 has a higher voltage headroom of 55 Volts, which advantageously enables the generation of stimulus signal sufficient to deliver 30 µA into the eye when used with the improved serpentine stimulus coil 200 of the present invention.

The improved pulse generator 220 is shown as a block diagram, which is similar to the prior pulse generator except that the digital potentiometer block used in the previous design has now been replaced with a switch/resistor bank block. This circuit block change occurred because there are no digital potentiometers that can handle 55 V. Therefore, in the new circuit, the 5V from the battery is boosted to 55V using a new boost converter. This voltage is then down regulated to the desired value by using an adjustable low drop out (LDO) voltage regulator and a switch/resistor bank, which determined the output of the LDO. The output voltage from the LDO is then fed to the H-bridge, which was used to drive the primary coil 222. The primary coil 222, in turn, transmits the signal to the improved serpentine stimulus coil 200 (Coil S4) to reduce IOP in the patient as described above.

The firmware on the microcontroller and the software for the graphical user interface (GUI) were updated to handle the increased capabilities of the improved pulse generator 220. The main reason for this was because the digital potentiometer was replaced by the switch/resistor bank. In the GUI for the new pulse generator, the user can pick the current that will be delivered to the eye from a drop-down menu which is determined by based on the coil-to-coil distance and the initial desired test currents. Additionally, the code for the microcontroller that drove the H-bridge in the prior pulse generator needed to be modified slightly since we incorporated a new part. Once the software and firmware changes were complete, we tested the new pulse generator to confirm its functionality.

FIG. 16 illustrates (on the left) a biphasic rectangular pulse 240 generated by the improved pulse generator 220 and (on the right) the resulting waveform 250 received by the improved serpentine stimulus coil 200 of the present invention. To test the improved pulse generator 220 of the present invention, it was connected to an oscilloscope to measure the output waveform 240, which can be seen on the left in FIG. 16. The improved pulse generator 220 was able to successfully create the biphasic rectangular pulse 240 which is used to drive the primary coil 222. It can be seen that the pulse generator 220 can also create voltage pulses greater than 27 V. The output of the pulse generator 220 was also connected to the primary coil 222 of FIG. 15, which was placed above a secondary coil (such as, by way of example only, the improved serpentine stimulus coil 200 of the present invention). The voltage measured across the secondary coil 200 can be seen in the waveform 250 on the right in FIG. 16. Importantly, the waveform 250 as generated by the improved pulse generator 220 matches the waveform obtained when using the old pulse generator. These initial tests verify the performance of the improved pulse generator 220.

FIGS. 17-19 are charts illustrating the improvements generated through the use of the improved pulse generator 220 of the present invention over a range (by way of example only) of input voltages of 3 volts to 27 volts in 3-volt increments. Namely, FIG. 17 shows the currents measured through saline at a distance of 10 mm from the primary coil 222 according to the present invention. FIG. 18 shows the currents measured through saline at a distance of 7 mm from the primary coil 222 according to the present invention. FIG. 19 shows the currents measured through saline at a distance of 7 mm from the prior pulse generator as described in the '691 Provisional. A comparison of FIGS. 18 and 19 reveal a dramatic increase in the currents generated by the improved pulse generator 220 (FIG. 18) relative to those generated by the prior pulse generator of the '691 Provisional (FIG. 19).

The various embodiments set forth herein may use different reference numerals throughout the drawings and specification when referring to the same or similar components, features and functionality in other or prior embodiments. Notwithstanding those differences in numbering, it will be appreciated that the disclosures of the various embodiments may be incorporated into the disclosures of the same or similar embodiments so as to facilitate the understanding and appreciation of the many features, functions and inventive aspects within this disclosure.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In addition, the actions recited in the claims can be performed in a different order and still achieve desirable results.

What is claimed is:

1. A device for reducing elevated intraocular pressure in an eye of a mammalian subject, comprising:
   a stimulation electrode assembly adapted to be positioned at least one of on, within and near the eye of the mammalian subject, wherein:
   the stimulation electrode assembly includes:
      at least one serpentine trace with a plurality of inner peaks to enable the stimulation electrode assembly to assume a 3-dimensional shape to facilitate placement over the eye of the mammalian subject,
      a plurality of inner electrodes positioned at the plurality of inner peaks of the serpentine trace and creating an inner circular shape,
      a plurality of outer electrodes creating an outer circular shape and being radially spart from the plurality of inner electrodes, and
      at least one serpentine trace to enable the stimulation electrode assembly to assume a 3-dimensional shape to facilitate placement over the eye of the mammalian subject, and
   the stimulation electrode assembly is adapted to deliver a stimulation signal to at least one intraocular structure in a therapeutically effective amount to reduce the elevated intraocular pressure within a mammalian eye by:
      (i) decreasing aqueous humor inflow into an anterior segment of the eye, and
      (ii) increasing aqueous humor outflow from the anterior segment of the eye.

2. The device of claim 1, wherein the plurality of inner electrodes and the plurality of outer electrodes are generally rectangular in shape.

3. The device of claim 1, wherein the stimulation electrode assembly comprises a plurality of serpentine traces, with an inner trace in contact with the inner electrodes and an outer trace in contact with the outer electrodes.

4. The device of claim 1, wherein the stimulation electrode assembly is a passive stimulation electrode adapted to receive an electromagnetic field from a signal generator and transmit the stimulation signal to the at least one intraocular structure to reduce the elevated intraocular pressure of the eye of the mammalian subject.

5. The device of claim 1, wherein the stimulation electrode assembly is part of a contact lens adapted to be positioned on the eye of the mammalian subject.

6. The device of claim 5, wherein the stimulation electrode assembly is positioned within the contact lens.

7. The device of claim 5, wherein the stimulation electrode assembly is positioned on an eye-contacting surface of the contact lens.

8. The device of claim 1, wherein the stimulation electrode assembly comprises
   a plurality of traces with an inner trace abutting the inner electrodes and an outer trace abutting the outer electrodes,
   wherein the inner trace includes multiple smaller serpentine curves connecting portions of the inner trace that abut the inner electrodes to portions of the inner trace that are spaced away from the inner electrodes and the outer trace includes multiple smaller serpentine curves connecting portions of the outer trace that abut the outer electrodes to portions of the outer trace that are spaced away from the outer electrodes.

* * * * *

UNITED STATES PATENT AND TRADEMARK OFFICE
CERTIFICATE OF CORRECTION

| | |
|---|---|
| PATENT NO. | : 11,191,962 B2 |
| APPLICATION NO. | : 16/351251 |
| DATED | : December 7, 2021 |
| INVENTOR(S) | : Pedro P. Irazoqui et al. |

It is certified that error appears in the above-identified patent and that said Letters Patent is hereby corrected as shown below:

In the Claims

In Column 15, Line 39, Claim 1, delete "spart" and insert -- apart --.

Signed and Sealed this
Seventh Day of February, 2023

*Katherine Kelly Vidal*

Katherine Kelly Vidal
*Director of the United States Patent and Trademark Office*